(12) United States Patent
Myerson et al.

(10) Patent No.: US 10,828,578 B2
(45) Date of Patent: Nov. 10, 2020

(54) REVERSIBLE CONTROL OF SOLUTION SOLUBILITY USING FUNCTIONALIZED NANOPARTICLES

(71) Applicant: Massachusetts Institute of Technology, Cambridge, MA (US)

(72) Inventors: Allan S. Myerson, Boston, MA (US); Samir Kulkarni, East Lyme, CT (US)

(73) Assignee: Massachusetts Institute of Technology, Cambridge, MA (US)

( * ) Notice: Subject to any disclaimer, the term of this patent is extended or adjusted under 35 U.S.C. 154(b) by 2 days.

(21) Appl. No.: 16/091,808

(22) PCT Filed: Apr. 6, 2017

(86) PCT No.: PCT/US2017/026348
§ 371 (c)(1),
(2) Date: Oct. 5, 2018

(87) PCT Pub. No.: WO2017/176995
PCT Pub. Date: Oct. 12, 2017

(65) Prior Publication Data
US 2019/0160392 A1    May 30, 2019

Related U.S. Application Data

(60) Provisional application No. 62/320,360, filed on Apr. 8, 2016.

(51) Int. Cl.
*B01D 9/00* (2006.01)
*C01D 3/04* (2006.01)
(Continued)

(52) U.S. Cl.
CPC .......... *B01D 9/0054* (2013.01); *A61K 31/138* (2013.01); *A61K 31/192* (2013.01);
(Continued)

(58) Field of Classification Search
CPC ............... B01D 9/0054; B01D 9/0068; B01D 2009/0086; B01D 9/02; B01D 11/00;
(Continued)

(56) References Cited

U.S. PATENT DOCUMENTS 3,234,126 A * 2/1966 Bloch ...................... C02F 1/22
210/711
8,323,360 B2   12/2012 Baran et al.
(Continued)

OTHER PUBLICATIONS

Invitation to Pay Additional Fees dated Jun. 19, 2017 for Application No. PCT/US2017/026348.
(Continued)

*Primary Examiner* — Joseph W Drodge
(74) *Attorney, Agent, or Firm* — Wolf, Greenfield & Sacks, P.C.

(57) ABSTRACT

Aspects of the disclosure relate to methods and compositions of altering a solution through the use of readily retrievable agents (e.g., a nanoparticle) having one or more functional groups configured to undergo a solvation interaction with a component of the solution. Compositions, systems, and methods for crystallizing organic and inorganic compounds from solutions using nanoparticles surface coated with functional groups that create a supersaturated state in the solution and reversal thereof. Compositions, systems, and methods for purifying water or active pharmaceutical ingredients. Compositions, systems, and methods for increasing the solubility of a solution and reversal of the same. Compositions, systems, and methods for decreasing the solubility of a crystallized compound and reversal of the same.

10 Claims, 22 Drawing Sheets

(51) Int. Cl.

| | | |
|---|---|---|
| C30B 29/54 | (2006.01) | |
| C30B 29/58 | (2006.01) | |
| C30B 7/14 | (2006.01) | |
| C30B 29/12 | (2006.01) | |
| A61K 31/13 | (2006.01) | |
| A61K 31/19 | (2006.01) | |
| A61K 31/16 | (2006.01) | |
| C02F 1/52 | (2006.01) | |
| C07K 1/30 | (2006.01) | |
| B01D 11/02 | (2006.01) | |
| B82Y 30/00 | (2011.01) | |
| A61K 31/138 | (2006.01) | |
| A61K 31/192 | (2006.01) | |
| A61K 31/216 | (2006.01) | |
| B82Y 25/00 | (2011.01) | |
| B82Y 40/00 | (2011.01) | |
| C02F 101/30 | (2006.01) | |

(52) U.S. Cl.
CPC .......... *A61K 31/216* (2013.01); *B01D 9/0068* (2013.01); *B01D 11/02* (2013.01); *B82Y 30/00* (2013.01); *C01D 3/04* (2013.01); *C02F 1/52* (2013.01); *C07K 1/306* (2013.01); *C30B 7/14* (2013.01); *C30B 29/12* (2013.01); *C30B 29/54* (2013.01); *C30B 29/58* (2013.01); *B01D 2009/0086* (2013.01); *B82Y 25/00* (2013.01); *B82Y 40/00* (2013.01); *C02F 2001/5218* (2013.01); *C02F 2101/30* (2013.01); *C02F 2305/08* (2013.01)

(58) Field of Classification Search
CPC ..... B01D 11/02; B01D 11/0288; B01D 11/04; B01D 11/0411; B01D 11/0492; B01D 2209/0086; B01D 2209/009; B01D 2209/0095; C30B 29/54; C30B 7/14; C30B 29/12; C30B 29/58; C30B 7/00; C30B 7/02; C30B 7/04; C30B 7/06; C30B 7/08; C02F 1/52; C02F 2101/30; C02F 2001/5218; C02F 2305/08; C02F 1/26; C02F 2103/343; A61K 31/138; A61K 31/192; A61K 31/216; C07K 1/306; C01D 3/04; B82Y 30/00; B82Y 40/00; B82Y 25/00; C09K 2208/10; C09K 8/52; C09K 2208/12
USPC ..... 117/4, 5, 11, 35; 210/634, 638, 639, 774
See application file for complete search history.

(56) References Cited

U.S. PATENT DOCUMENTS

| | | | |
|---|---|---|---|
| 2006/0096523 A1 | 5/2006 | Myerson et al. | |
| 2007/0087400 A1* | 4/2007 | Darzins .................. | B82Y 30/00 435/25 |
| 2011/0077392 A1* | 3/2011 | Baran, Jr. ............. | A61K 9/1688 536/123.13 |
| 2012/0018382 A1* | 1/2012 | Stein ........................ | B03C 1/01 210/663 |
| 2013/0090459 A1 | 4/2013 | Aslan | |
| 2013/0195767 A1 | 8/2013 | Weissleder et al. | |
| 2017/0362282 A1* | 12/2017 | Snow .................. | C07K 14/005 |

OTHER PUBLICATIONS

International Search Report and Written Opinion dated Aug. 25, 2017 for Application No. PCT/US2017/026348.
International Preliminary Report on Patentability dated Oct. 18, 2018 for Application No. PCT/US2017/026348.
Bucak et al., Protein separations using colloidal magnetic nanoparticles. Biotechnol Prog. Jan. 2003;19(2):477-84. Epub Nov. 16, 2002.
Kulkarni et al., Reversible control of solubility using functionalized nanoparticles. Chem Commun. 2017;53:1429-32. Epub Dec. 12, 2016.
Pandey et al., Cationic poly (lactic-co-glycolic acid) iron oxide microspheres for nucleic detection. Nanoscale. 2013;5:3800-7. Epub Feb. 12, 2013.
Extended European Search Report for EP App No. 17779820.4 dated Feb. 19, 2020.
Partial supplementary European Search Report for EP App No. 17779820.4 dated Oct. 31, 2019.
[No Author Listed] Nanopartz™ Gold Nanoparticles for Analytical Applications. Jan. 5, 2016. Retrieved from https://web.archive.org/web/20160105043423/http://www.nanopartz.com:80/analytical_gold_nanoparticles.asp. On Oct. 22, 2019.
Ballerstadt et al., Fiber-coupled fluorescence affinity sensor for 3-day in vivo glucose sensing. J Diabetes Sci Technol. May 2007;1(3):384-93.
Giljohann et al., Gold nanoparticles for biology and medicine. Angew Chem Int Ed Engl. Apr. 26, 2010;49(19):3280-94. doi: 10.1002/anie.200904359.
Kolb et al., Click Chemistry: Diverse Chemical Function from a Few Good Reactions. Angew Chem Int Ed Engl. Jun. 1, 2001;40(11):2004-2021.
Kolb et al., The growing impact of click chemistry on drug discovery. Drug Discov Today. Dec. 15, 2003;8(24):1128-37.
Lee et al., A potent and highly selective inhibitor of human alpha-1,3-fucosyltransferase via click chemistry. J Am Chem Soc. Aug. 13, 2003;125(32):9588-9.
Lewis et al., Click chemistry in situ: acetylcholinesterase as a reaction vessel for the selective assembly of a femtomolar inhibitor from an array of building blocks. Angew Chem Int Ed Engl. Mar. 15, 2002;41(6):1053-7.
Love et al., Self-assembled monolayers of thiolates on metals as a form of nanotechnology. Chem Rev. Apr. 2005;105(4):1103-69.
Manetsch et al., In situ click chemistry: enzyme inhibitors made to their own specifications. J Am Chem Soc. Oct. 13, 2004;126(40):12809-18.
Mocharla et al., In situ click chemistry: enzyme-generated inhibitors of carbonic anhydrase II. Angew Chem Int Ed Engl. Dec. 17, 2004;44(1):116-20.
Rana et al., Monolayer coated gold nanoparticles for delivery applications. Adv Drug Deliv Rev. Feb. 2012;64(2):200-16. doi:10.1016/j.addr.2011.08.006. Epub Sep. 6, 2011.
Rostovtsev et al., A stepwise huisgen cycloaddition process: copper(I)-catalyzed regioselective "ligation" of azides and terminal alkynes. Angew Chem Int Ed Engl. Jul. 15, 2002;41(14):2596-9.
Tiwari et al., Functionalized Gold Nanoparticles and Their Biomedical Applications. Nanomaterials (Basel). Jun. 14, 2011;1(1):31-63. doi: 10.3390/nano1010031.
Tornøe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.
Van Lehn et al., Effect of particle diameter and surface composition on the spontaneous fusion of monolayer-protected gold nanoparticles with lipid bilayers. Nano Lett. Sep. 11, 2013;13(9):4060-7. doi: 10.1021/nl401365n. Epub Aug. 20, 2013.
Verma et al., Surface-structure-regulated cell-membrane penetration by monolayer-protected nanoparticles. Nat Mater. Jul. 2008;7(7):588-95. doi: 10.1038/nmat2202. Epub May 25, 2008. Erratum in: Nat Mater. Apr. 2013;12(4):376.
Wang et al., Bioconjugation by copper(I)-catalyzed azide-alkyne [3+2] cycloaddition. J Am Chem Soc. Mar. 19, 2003;125(11):3192-3.

* cited by examiner ural patent application number PCT/
REVERSIBLE CONTROL OF SOLUTION SOLUBILITY USING FUNCTIONALIZED NANOPARTICLES

RELATED APPLICATIONS

This application is a national stage filing under 35 U.S.C. § 371 of international patent application number PCT/US2017/026348, filed Apr. 6, 2017, and claims the benefit under 35 U.S.C. § 119(e) of U.S. provisional application Ser. No. 62/320,360, filed Apr. 8, 2016, the entire contents of each of which is incorporated herein by reference.

BACKGROUND

Dissolution of solids or their crystallization/precipitation from solution is a fundamental process employed in a wide variety of industries and laboratories. Methods to change the solubility of a solid in a solution include temperature change, pH change, and change in the solvent composition. Normally a change in the solvent composition involves the mixing of two solvents and thus this change in composition is not reversible.

Crystallization is an important separation and purification technique, which is essential in many processes in chemical industries, ranging from bulk chemicals to special products. An industrial crystallization has to be carefully controlled in order to meet crystal product quality demands, e.g., crystal form, particle size distribution, crystal shape, and purity. Crystal quality depends heavily on the process conditions under which crystal nucleation occurs. Many factors e.g., supersaturation, temperature, type of antisolvent, and heterogeneous particles influence the nature of the crystallized polymorph and physiochemical properties of solids.

SUMMARY

Aspects of the disclosure relate to methods and compositions of altering a solution (e.g., solubility conditions of the solution). Traditionally, the solubility conditions of solutions have been manipulated using co-solvent techniques that involve combining one or more co-solvents with the solution to affect its properties. While such methods may be useful for either increasing or decreasing the apparent solubility of solutes in solution (e.g., to modulate crystallization processes), subsequent separation of solvents and co-solvents can often involve difficult or involved downstream processes that can drive up processing time and costs. In contrast, in some embodiments, methods provided herein involve the use of agents that can be added to solutions to modulate solubility for a period of time, and then can be readily retrieved from the solution. For example, certain methods provided herein involve combining a solution with a readily retrievable agent (e.g., a nanoparticle) having one or more functional groups configured to undergo a solvation interaction with a component of the solution. In some embodiments, the solvation interaction is solvation of the one or more functional groups by the solvent, which surprisingly results in a reduction in the apparent solubility of a solute in the solution (e.g., which may promote crystallization, as shown in Examples 7, 9, 11, 12, and 14 herein). However, in some embodiments, the solvation interaction is solvation of a solute of the solution by the one or more functional groups, which surprisingly results in an increase in the apparent solubility of a solute in the solution (e.g., as shown in Examples 15 and 16 herein). In some embodiments, the readily retrievable agent is a nanoparticle (e.g., a magnetic nanoparticle). In some embodiments, the readily retrievable agent is surface coated with the one or more functional groups. In some embodiments, the readily retrievable agent further comprises one or more affinity tags. In some embodiments, the affinity tag comprises a streptavidin or biotin moiety. In some embodiments, the methods further comprise: i) maintaining the combination for a period of time; and ii) following step i), retrieving the readily retrievable agent from the solution.

According to some aspects of the disclosure, methods are provided for adjusting solubility to control crystallization conditions. For example, in some embodiments, methods are provided for inducing crystallization. In other embodiments, methods are provided to dissolve crystals or inhibit crystallization. In some embodiments, methods are provided herein for reversibly changing solubility to induce crystallization or to dissolve crystals or inhibit crystallization (e.g., without a permanent change to the solvent composition) through the use of functionalized nanoparticles.

In some embodiments, methods for crystallizing compounds (e.g., chemical or pharmaceutical compounds) are provided. In some embodiments, crystallization methods provided herein utilize an unique process to antisolvent crystallization. In some embodiments, functionalized nanoparticles are used to crystallize organic and inorganic chemical and pharmaceutical compounds. In some embodiments, the functionalized nanoparticles do not act as a template to crystallize but produce supersaturation conditions by decreasing the solubility of organic or inorganic compounds in solution. Thus, in some embodiments, self-assembled nanoparticles are used in the present disclosure as a replacement for antisolvents to carry out crystallization by decreasing the solubility of organic or inorganic compounds in the given solvent system. In some embodiments, a self-assembled nanoparticle is provided that is a metal nanoparticle, e.g., gold, metal oxide nanoparticle, and/or magnetic nanoparticle. In some embodiments, the compound, solvent type, and amount of functionalized nanoparticles relative to the solution are selected parameters that influence crystallization according to methods provided herein.

In some embodiments, the nanoparticles can be separated or removed from a supersaturated solution to reverse crystallization of the compound/solvent, such that the crystallized compound dissolves, transforming the solution to a saturated or undersaturated state. In some embodiments, functionalized nanoparticles with the same functional group as a co-solvent are used to increase the solubility of poorly soluble compounds. In some embodiments, the functionalized nanoparticles can be separated or removed from a solution to reverse solubility of the compound/solvent, in which solubility of the compound is decreased after the nanoparticles are removed.

According to some aspects of the disclosure, methods are provided to reversibly change solution solubility. In some embodiments, reversibly changing solution solubility induces crystallization. In some embodiments, reversibly changing solution solubility induces crystal dissolution or inhibition of crystallization. In some embodiments of the disclosure the methods provided do not cause a permanent change to the solvent composition. In other words, in some embodiments, methods provided herein are reversible.

According to some aspects, the disclosure relates to a method of producing crystals, the method comprising adding to a solution at a concentration at saturation or below saturation of the compound of interest an effective amount of nanoparticles surface coated with functional groups that reduce the solution solubility while remaining attached to the nanoparticles, wherein when present in the solution, the nanoparticles transform the solution to a supersaturated state causing nucleation and subsequent growth of crystals comprising constituents of the solution.

According to some aspects, the disclosure relates to a method of producing crystals, the method comprising adding to a solution comprising a compound of interest, an effective amount of nanoparticles surface coated with a solubility-lowering agent, wherein following addition of the nanoparticles to the solution, the solution is transformed to a supersaturated state causing nucleation and subsequent growth of crystals comprising the compound.

In some embodiments, the compound of interest is an organic compound. In some embodiments, the compound of interest is an inorganic compound. In some embodiments, before addition of the nanoparticles to the solution, the solution is not supersaturated. In some embodiments, the solubility-lowering agent is a functional group that remains attached to the nanoparticle when present in the solution.

In some embodiments, the nanoparticle comprises a metal. In some embodiments, the metal is selected from: aluminum, beryllium, bismuth, cadmium, carbon, cobalt, copper, germanium, gold, hafnium, indium, iridium, iron, lead, magnesium, molybdenum, nickel, niobium, palladium, platinum, rhenium, rhodium, silicon, silver, tantalum, tin, titanium, tungsten, vanadium, zinc, and zirconium. In some embodiments, the metal is in a substantially pure form. In some embodiments, the metal is in the form of a metal oxide. In some embodiments, the metal oxide is a silver oxide, iron oxide, or silicon dioxide. In some embodiments, the metal is gold. In some embodiments, the nanoparticle is magnetic. In some embodiments, the nanoparticle is paramagnetic. In some embodiments, the solubility-lowering agent comprises a thiol, a carboxyl, or a hydroxyl group. In some embodiments, the nanoparticle is functionalized with an attaching group that attaches the functional group to the nanoparticle via a backbone.

In some embodiments, the nanoparticle is functionalized with a self-assembled monolayer (SAMs). In some embodiments, the SAMs include a thiol and/or silane based surfactant molecule. In some embodiments, the SAM is selected from: short and long chain alkanethiols, $SH(CH_2)_nX$, and aromatic thiolates, $SH(C_6HS)_nX$, where n represents chain length, wherein n may be 1, 2, 3, 4, 5, 6, 7, 8, 9, 10 or more and X represents an organic and inorganic functional tail group. In some embodiments, the functional tail group is selected from: $CO_2^-$, $SO_3^-$, $PO_3^-$, $NH_3^+$, $N(CH_3)_3^+$, $NO_2$, OH, $CH_3$, $CF_3$, F, Cl, Br, I, $CO_2CH_3$, SH, $C_2H_4OH$ and $SCH_3$.

In some embodiments, the nanoparticle is approximately spherical. In some embodiments, the nanoparticle is less than 10 nm in average diameter. In some embodiments, the nanoparticle is approximately 1 nm to 10 nm in average diameter. In some embodiments, the gold nanoparticles are coated with 2-mercaptoethanol. In some embodiments, the nanoparticle is spherical and the surface area per nanoparticle in the solution is approximately $4\pi r^2$, wherein r denotes radius of the nanoparticle. In some embodiments, the surface area of nanoparticles per unit volume of solution is in the range of 1 nm nanoparticles/ml solution to 100 nm nanoparticles/ml solution. In some embodiments, the surface area of nanoparticles per unit volume of solution is about 1, 2, 3, 4, 5, 7, 10, 15, 20, 25, 30, 35, 40, 45, 50, 60, 70, 80, 90, or 100 nm nanoparticles/ml solution. In some embodiments, the surface area of nanoparticles per unit volume of solution is about 1-5 nm nanoparticles/ml solution, 1-10 nm nanoparticles/ml solution, 5-10 nm nanoparticles/ml solution, 1-20 nm nanoparticles/ml solution, 5-20 nm nanoparticles/ml solution, 10-20 nm nanoparticles/ml solution, 10-50 nm nanoparticles/ml solution, 25-50 nm nanoparticles/ml solution, 30-50 nm nanoparticles/ml solution, 20-40 nm nanoparticles/ml solution, 30-60 nm nanoparticles/ml solution, 40-60 nm nanoparticles/ml solution, 50-75 nm nanoparticles/ml solution, 60-80 nm nanoparticles/ml solution, 50-100 nm nanoparticles/ml solution, 60-100 nm nanoparticles/ml solution, or 75-100 nm nanoparticles/ml solution. In some embodiments, the density of nanoparticles in the solution is approximately 0.1 g nanoparticle/ml to 30 g nanoparticles/ml solution. In some embodiments, the density of nanoparticles in the solution is about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 g nanoparticle/ml. In some embodiments, the density of nanoparticles in the solution is about 0.1-1 g nanoparticle/ml, 0.5-1 g nanoparticle/ml, 1-2 g nanoparticle/ml, 1-5 g nanoparticle/ml, 1-10 g nanoparticle/ml, 5-10 g nanoparticle/ml, 5-15 g nanoparticle/ml, 10-15 g nanoparticle/ml, 10-20 g nanoparticle/ml, 15-20 g nanoparticle/ml, 15-25 g nanoparticle/ml, 20-25 g nanoparticle/ml, 20-30 g nanoparticle/ml, or 25-30 g nanoparticle/ml. In some embodiments, the compound of interest comprises an active pharmaceutical ingredient (API), a salt, or a biological macromolecule. In some embodiments, the compound of interest comprises a protein, NaCl, fenofibrate, diphenhydramine, ibuprofen, or D-mannitol. In some embodiments, the crystals comprising the compound of interest are separated from the solution.

In some embodiments, the nanoparticles are separated from the solution by a magnet. In some embodiments, the crystals comprising the compound of interest are separated from the solution by centrifugation. In some embodiments, the crystals comprising the compound of interest are separated from the solution by filtration. In some embodiments, the method further comprises removal of the nanoparticles to reverse crystallization and cause solubilization.

According to some aspects, the disclosure relates to a system for producing crystals, the system comprising a first container housing a solution comprising a compound of interest, and a second container housing nanoparticles surface coated with a solubility-lowering agent. In some embodiments, the system further comprises an apparatus for transferring an effective amount of the nanoparticles to the solution. In some embodiments, an effective amount is an amount that may produce in the solution a supersaturated state. In some embodiments, in the supersaturated state, crystals comprising the compound of interest are formed in the solution.

According to some aspects, the disclosure relates to a composition comprising i) a solution that comprises a dissolved compound, and ii) nanoparticles surface coated with a solubility-lowering agent, wherein the nanoparticles are present in an amount effective for producing in the solution a supersaturated state to nucleate and grow crystals comprising the compound. In some embodiments, the nanoparticles are suspended in the solution. In some embodiments, the nanoparticles are suspended in the solution by mixing.

According to some aspects, the disclosure relates to a method of crystallizing a compound, comprising: preparing at room temperature a saturated solution comprising a compound of interest, mixing or stirring the solution, e.g., for at least 24 hours, filtering the saturated solution to obtain a filtrate, diluting the filtrate with a solvent to create an undersaturated solution, adding an effective amount of nanoparticles surface coated with a solubility-lowering agent to the undersaturated solution, mixing the solution and nanoparticles to produce a slurry of crystals comprising the compound, and recovering the crystals. In some embodiments, the compound is an organic compound. In some embodiments, the compound is an inorganic compound. In some embodiments, an effective amount is one that increases saturation of the solution. In some embodiments, the crystals are recovered by filtration or centrifugation. In some embodiments, when magnetic nanoparticles are used, the nanoparticles in the solution are first separated from the solution and the slurry of crystals, using a magnet, before the crystals are recovered.

According to some aspects, the disclosure relates to a method for purifying an impure solution, wherein a column comprises an effective amount of nanoparticles surface coated with a solubility-lowering agent, a first opening, and a second opening, comprising adding the impure solution to the column through the first opening and allowing a purified solution to exit the column through the second opening. In some embodiments, the impure solution comprises water. In some embodiments, the purified solution is water. In some embodiments, crystals of unwanted solids, chemicals, and particulates of the impure solution form inside the column.

According to some aspects, the disclosure relates to a system for purifying an impure solution, the system comprising: a first container housing a column and solubility-lowering nanoparticles, wherein the column comprises an effective amount of the nanoparticles, an apparatus for transferring solution into the column, and an apparatus to allow exit of a solution from the column, wherein the solution that enters the column is impure and the solution that exits the column is in a substantially pure form. In some embodiments, the solution that enters the column comprises water. In some embodiments, the solution that exits the column is water. In some embodiments, crystals of unwanted solids, chemicals, and particulates of the impure solution form inside the column after adding the impure solution to the column.

According to some aspects, the disclosure relates to a method for purifying an impure solution, wherein a column comprises an effective amount of nanoparticles surface coated with a solubility-lowering agent, a first opening, and a second opening, comprising: delivering the impure solution to the column through the first opening, allowing impurities to exit the column through the second opening, adding a solvent to the column through the first opening, and allowing a dissolved solution to exit the column through the second opening, wherein the solvent dissolves crystals comprising the compound of interest that formed inside the column in the presence of the nanoparticles and wherein the dissolved solution comprises the purified compound of interest. In some embodiments, the impure solution comprises an active pharmaceutical ingredient (API). In some embodiments, the compound of interest is an API. In some embodiments, the purified compound of interest is an API. In some embodiments, the impurities comprise unwanted solids, chemicals, and/or particulates of the impure solution. In some embodiments, the purified compound is crystallized outside of the column.

According to some aspects, the disclosure relates to a system for purifying a solution, the system comprising a first container housing a column comprising at least two openings and nanoparticles surface coated with a solubility-lowering agent, wherein the column comprises an effective amount of the nanoparticles. In some embodiments, the system further comprises an apparatus for transferring to the column an impure solution comprising a compound of interest, an apparatus for transferring a second solvent into the column, an apparatus to allow exit of impurities from the column, and an apparatus to allow exit of a purified solution comprising the compound of interest from the column.

In some embodiments, the impure solution comprises an API. In some embodiments, the purified solution that exits the column comprises a substantially pure API. In some embodiments, the impurities comprise unwanted solids, chemicals, and/or particulates of the impure solution. In some embodiments, the compound of interest may be crystallized from the purified solution outside of the column.

According to some aspects, the disclosure relates to a composition comprising a nanoparticle surface coated with a solubility-lowering agent. In some embodiments, the solubility-lowering agent is a functional group attached to the nanoparticle. In some embodiments, the nanoparticle comprises a metal. In some embodiments, the metal is selected from: aluminum, beryllium, bismuth, cadmium, carbon, cobalt, copper, germanium, gold, hafnium, indium, iridium, iron, lead, magnesium, molybdenum, nickel, niobium, palladium, platinum, rhenium, rhodium, silicon, silver, tantalum, tin, titanium, tungsten, vanadium, zinc, and zirconium. In some embodiments, the metal is in a substantially pure form. In some embodiments, the metal is in the form of a metal oxide. In some embodiments, the metal oxide is a silver oxide, iron oxide, or silicon dioxide. In some embodiments, the metal is gold. In some embodiments, the nanoparticle is magnetic. In some embodiments, the nanoparticle is paramagnetic. In some embodiments, the solubility-lowering agent comprises a thiol comprises a thiol, a carboxyl, or a hydroxyl group. In some embodiments, the nanoparticle is functionalized with an attaching group that attaches the functional group to the nanoparticle via a backbone. In some embodiments, the nanoparticle is a core shell nanoparticle as is described herein.

In some embodiments, the nanoparticle is functionalized with a self-assembled monolayer (SAMs), as is described herein. In some embodiments, the SAMs include a thiol and/or silane based surfactant molecule. In some embodiments, the SAM is selected from: short and long chain alkanethiols, $SH(CH_2)_nX$, and aromatic thiolates, $SH(C_6HS)_nX$, where n represents chain length, wherein n may be 1, 2, 3, 4, 5, 6, 7, 8, 9, 10 or more and X represents an organic and inorganic functional tail group. In some embodiments, the functional tail group is selected from: $CO_2^-$, $SO_3^-$, $PO_3^-$, $NH_3^+$, $N(CH_3)_3^+$, $NO_2$, $OH$, $CH_3$, $CF_3$, $F$, $Cl$, $Br$, $I$, $CO_2CH_3$, $SH$, $C_2H_4OH$ and $SCH_3$. In some embodiments, the amount of solubility-lowering agent on the nanoparticle is present in an effective amount. In some embodiments, the nanoparticle is approximately spherical. In some embodiments, the nanoparticle is less than 10 nm in diameter or average diameter. In some embodiments, the nanoparticle is approximately 1 nm to 10 nm in diameter or average diameter, e.g., 1, 1.1, 1.2, 1.3, 1.4, 1.5, 1.6, 1.7, 1.8, 1.9, 2, 3, 4, 5, 6, 7, 8, 9, or 10 nm. In some embodiments, the gold nanoparticles are coated with 2-mercaptoethanol.

According to some aspects, the disclosure relates to a composition comprising a nanoparticle surface coated with an agent that increases the solubility of a solution.

According to some aspects, the disclosure relates to a method of increasing solution solubility, the method comprising adding to a solution or a slurry comprising a compound of interest, nanoparticles surface coated with functional groups that increase the solution solubility, wherein following addition of the nanoparticles to the solution, the solution solubility increases. In some embodiments, the solution comprises a co-solvent. In some embodiments, the co-solvent is glycerin, propylene glycol, polyethylene glycol 300, polyethylene glycol 400, or ethanol.

According to some aspects, the disclosure relates to a method of modulating solution solubility, comprising i.) providing a solution (e.g., an undersaturated, saturated, or supersaturated solution, or a slurry, which comprises a solution and undissolved solids); ii.) adding to the solution functionalized nanoparticles that reduce solubility or inhibit crystallization of a component of the solution; iii.) maintaining the functionalized nanoparticles in the solution; and iv.) subsequent to step iii.) removing the functionalized nanoparticles from the solution to increase solubility or promote crystallization.

According to some aspects, the disclosure relates to a method comprising: i.) providing a solution (e.g., an undersaturated, saturated, or supersaturated solution), wherein the solution comprises crystals; ii.) adding to the solution functionalized nanoparticles that reduce solubility of a component of the solution; iii.) maintaining the functionalized nanoparticles in the solution under conditions that enable the crystals to dissolve in the solution; and iv.) subsequent to step iii.) removing the functionalized nanoparticles from the solution.

According to some aspects, the disclosure relates to a method comprising adding nanoparticles surface coated with functional groups that increase solution solubility to a solution that comprises crystals comprising a compound of interest, wherein following addition of the nanoparticles to the solution, the crystals dissolve in the solution. In some embodiments, the method increases solubility. In some embodiments, method inhibits crystal formation. In some embodiments, the solution comprises a co-solvent. In some embodiments, the co-solvent is glycerin, propylene glycol, polyethylene glycol 400, polyethylene glycol 300, or ethanol. In some embodiments, the compound of interest is an organic compound. In some embodiments, the compound of interest is an inorganic compound. In some embodiments, before addition of the nanoparticles to the solution, the solution is undersaturated. In some embodiments, before addition of the nanoparticles to the solution, the solution is saturated. In some embodiments, before addition of the nanoparticles to the solution, the solution is supersaturated. In some embodiments, the functional group remains attached to the nanoparticle when present in the solution.

In some embodiments, the nanoparticle comprises a metal. In some embodiments, the metal is selected from: aluminum, beryllium, bismuth, cadmium, carbon, cobalt, copper, germanium, gold, hafnium, indium, iridium, iron, lead, magnesium, molybdenum, nickel, niobium, palladium, platinum, rhenium, rhodium, silicon, silver, tantalum, tin, titanium, tungsten, vanadium, zinc, and zirconium. In some embodiments, the metal is in a substantially pure form. In some embodiments, the metal is in the form of a metal oxide. In some embodiments, the metal oxide is a silver oxide, iron oxide, or silicon dioxide. In some embodiments, the metal is gold. In some embodiments, the nanoparticle is magnetic. In some embodiments, the functional group is a thiol, a carboxyl, or a hydroxyl group.

In some embodiments, the nanoparticle is approximately spherical. In some embodiments, the nanoparticle is a disk, a rod, or a planer particle. In some embodiments, the nanoparticle is a particle with a rough or convoluted surface. In some embodiments, the nanoparticle is less than 10 nm in average diameter. In some embodiments, the nanoparticle is approximately 1 nm to 10 nm in average diameter. In some embodiments, the gold nanoparticles are coated with 2-mercaptoethanol. In some embodiments, the nanoparticle is spherical and the surface area per nanoparticle in the solution is approximately $4 \pi r^2$, wherein r denotes radius of the nanoparticle. In some embodiments, the surface area of nanoparticles per unit volume of solution is in the range of 1 nm nanoparticles/ml solution to 100 nm nanoparticles/ml solution. In some embodiments, the density of nanoparticles in the solution is approximately 0.1 g nanoparticle/ml to 30 g nanoparticles/ml solution. In some embodiments, the nanoparticles are removed to reverse the solution solubility to a saturated or supersaturated state. In some embodiments, the co-solvent is glycerin, propylene glycol, polyethylene glycol 300, polyethylene glycol 400, or ethanol.

DETAILED DESCRIPTION

Figure 1:
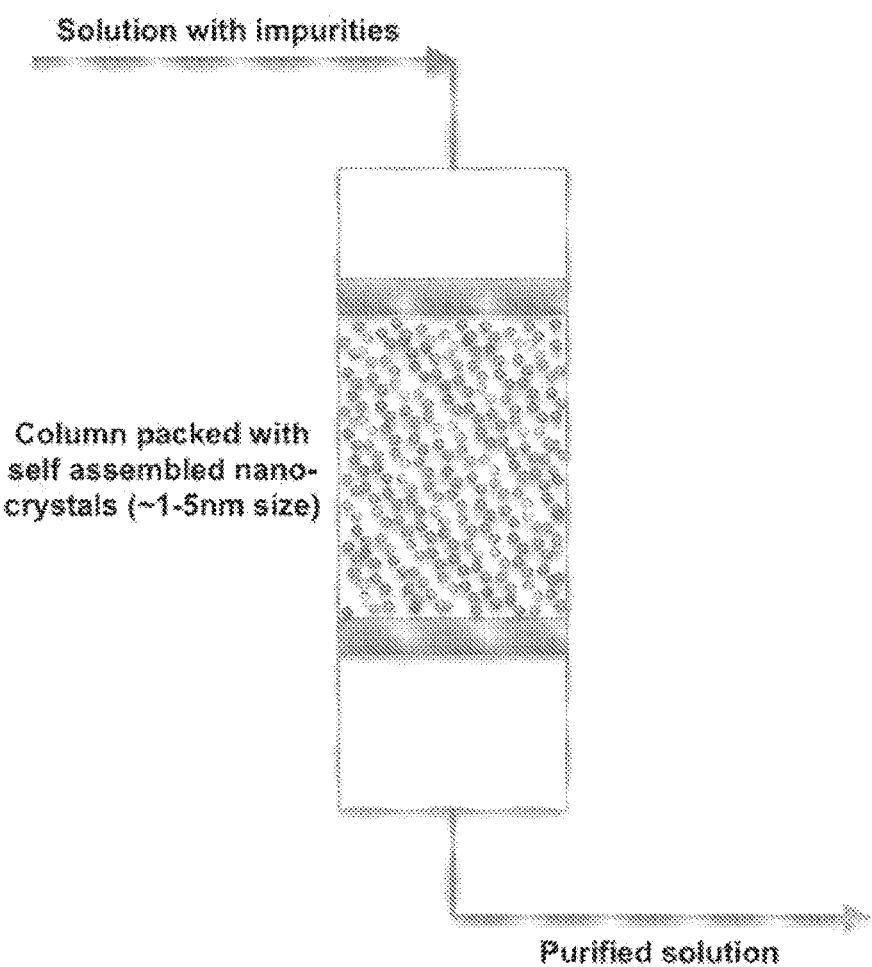
FIG. 1 is a schematic diagram of a water purification process using functionalized nanoparticles.

Provided herein are methods and compositions of altering a solution (e.g., solubility conditions of the solution). The present disclosure provides compositions, systems, and methods for controlling crystallization of organic and inorganic compounds (e.g., in solutions that are not supersaturated). In some embodiments, methods are provided for increasing the solubility of organic or inorganic compounds and/or for crystallization or solubilization. In some embodiments, methods provided herein involve the use of agents that can be added to solutions to modulate solubility for a period of time, and then can be readily retrieved from the solution. For example, certain methods provided herein involve combining a solution with a readily retrievable agent (e.g., a nanoparticle) having one or more functional groups configured to undergo a solvation interaction with a component of the solution. In some embodiments, the solvation interaction is solvation of the one or more functional groups by the solvent, which surprisingly results in a reduction in the apparent solubility of a solute in the solution (e.g., which may promote crystallization, as shown in Examples 7, 9, 11, 12, and 14 herein). However, in some embodiments, the solvation interaction is solvation of a solute of the solution by the one or more functional groups, which surprisingly results in an increase in the apparent solubility of a solute in the solution (e.g., as shown in Examples 15 and 16 herein). A readily retrievable agent is an agent that can be delivered to solution and readily removed, as compared with a miscible or immiscible solvent. In some embodiments, a readily retrievable agent comprises an insoluble core with one or more functional groups suspended in solution. In some embodiments, a readily retrievable agent comprises a nanoparticle.

In some embodiments, methods provided herein use an effective amount of nanoparticles surface coated with a functional group or a solubility-lowering agent, also referred to as functionalized or multi-functionalized nanoparticles. Also disclosed, in some embodiments, are functionalized nanoparticles with the same functional group as a selected co-solvent to increase the solubility of poorly soluble compounds. In some embodiments, the functionalized nanoparticles can be removed from the solution to reverse the saturation induced by the functionalized nanoparticles, for example, to allow crystals comprising a compound to dissolve back into solution or to cause re-crystallization of a solubilized compound, in which an effective amount of functionalized nanoparticles caused crystallization of the compound comprised in the solution or solubilization of the compound comprised in the solution, respectively.

Solubility is a capacity or ability of a chemical substance, referred to as a solute, to dissolve in a solvent to form a solution of the solute in that solvent. In some embodiments, the solubility of a substance depends on the solvent or solvent mixture used as well as on temperature and pressure. A solution is in the saturated state when the chemical potential of the solid phase is the same as that of the dissolved species in solution. In some embodiments, changing the solid form (polymorph) of a crystalline solid thus can change the solubility as the solid phase has a different chemical potential. In some embodiments, in order to control the solubility of a solution the solvent composition can be altered. In some embodiments, this is done by changing the composition of the solvent by addition of another solvent where the two solvents are miscible. In some embodiments, this can result in an increase or decrease in the solubility. In some embodiments, when this is done in crystallization processes, this is often known as antisolvent addition. In some embodiments, changing the solvent composition however is not easily reversible and would involve additional processing steps for solvent recovery. In some embodiments, methanol injection undersea oil pipelines is a method to prevent the formation of gas hydrate crystals and works by increasing the solubility of the gas hydrates crystals in the methanol-water mixture (compared to the water alone). In some embodiments, however, methanol injection carries a high health, safety, and environment (HSE) risk and must be recovered from the seawater via distillation or extraction. In some embodiments, there is a need for an alternative method to prevent hydrate formation. In some embodiments, functionalized nanoparticles are used that have the same functional group as a co-solvent to increase the solubility of a particular compound. In some embodiments, methanol-functionalized nanoparticles can be a better choice to replace methanol in order to prevent gas hydrates in gas industry. Nanoparticles can be more effective and they carry a lower health, safety, and environment (HSE) risk as compared to methanol solvent.

The process of antisolvent crystallization is widely used in the chemical and pharmaceutical industries for the separation, purification, and production of bulk or fine chemicals. The limitations of known antisolvent crystallization approaches include higher supersaturation gradients within the solution. They also require additional costs associated with the solvent separation and large capital costs are required due to the higher operating volume. Thus, aspects of the disclosure relate to a recognition that a need exists for an improved crystallization process and systems to produce crystals with high quality (crystal size, morphology, polymorphs) and yields. Further, aspects of the disclosure relate to a recognition that a need exists for crystallization processes that produce the product that are sensitive to degradation by heating.

In some embodiments, the disclosure relates to antisolvent crystallization techniques. In some embodiments, the process of antisolvent crystallization is used in the chemical and pharmaceutical industries for the separation, purification, and production of bulk or fine chemicals. In some embodiments, in antisolvent crystallization, a state of supersaturation is generated by changing the solubility of the system by the addition of an antisolvent. In some embodiments, primary nucleation and subsequent crystallization occur in the supersaturated solution and not on the antisolvent. In some embodiments, self-assembled nanoparticles are used as a replacement for antisolvent, to carry out crystallization by decreasing the solubility of organic or inorganic compounds in the solution or solvent system. In some embodiments the self-assembled nanoparticles are gold and/or magnetic nanoparticles. In some embodiments, the present disclosure provides methods for crystallizing a compound of interest comprised in a solution using functionalized nanoparticles as an antisolvent. In some embodiments, primary nucleation and subsequent crystallization induced by the functionalized nanoparticles occurs in the solution, not on the nanoparticles, and not on a solid surface. Accordingly, in some embodiments, nanoparticles do not function as crystallization templates. Rather, in some embodiments, functionalized nanoparticles are added to a solution (e.g., an understaturated, saturated or supersaturated solution, or a slurry) to change the solubility of the solution (either increasing or decreasing solubility). In some embodiments, methods comprise preparing a saturated solution of a compound of interest by making a suspension of the compound in a corresponding solvent at an appropriate temperature (e.g., room temperature). In some embodiments, room temperature is approximately 20-25 degrees Celsius, e.g., 20, 21, 22, 23, 24, or 25. In some embodiments, the appropriate temperature is above 0 degrees Celsius to below 100 degrees Celsius. In some embodiments, the methods comprise preparing a saturated solution of a compound of interest by making a suspension of the compound in a corresponding liquid solvent at any temperature below the boiling point of the solvent. In some embodiments, the compound comprises an inorganic compound or an organic compound. Examples of compounds of the disclosure include, without limitation, APIs, salts, and macromolecules. In some embodiments, examples of compounds include, without limitation, benzoic acid, NaCl, fenofibrate, 4-nitrophenol, and D-mannitol. Other compounds are encompassed by the present disclosure. In some embodiments, the suspension is optionally mixed, stirred, or agitated and filtered, and a clear saturated solution as a filtrate is used. A filtrate is the solution that passes through a filter. In some embodiments, the clear saturated solution is diluted with solvent in order to create an undersaturated solution. Non-limiting examples of compounds or solutes and their solvents are included in Table 1. In some embodiments, an amount of functionalized nanoparticles is calculated corresponding to an amount, e.g., 1 ml, of antisolvent. In some embodiments, a clear undersaturated solution is mixed with a calculated amount of functionalized nanoparticles to reduce solubility. In some embodiments, an undersaturated, a saturated solution, a supersaturated solution, or a slurry is mixed with a calculated amount of functionalized nanoparticles to reduce solution solubility (e.g., to achieve undersaturated conditions). In some embodiments, the system is mixed or agitated to produce a slurry of crystals of organic and inorganic compounds. In some embodiments, crystals of organic or inorganic compounds are recovered from the slurry by filtration or centrifugation. In some embodiments, in which magnetic nanoparticles are used, a strong magnet may be utilized to separate the magnetic nanoparticles that are in the solution and the slurry is filtered to separate crystals comprising organic or inorganic compound from solution. In some embodiments, a filter used to separate the crystals comprises a pore size of 0.2 nm to 0.25 micron. In some embodiments, a filter used to separate the crystals comprises a pore size of up to 200 Da.

In some embodiments, for crystallization compositions, methods, and systems, the functional group or solubility-lowering agent attached to the nanoparticle can reduce solution solubility while remaining attached to the nanoparticle, wherein when present in the solution, the nanoparticles transform the solution to a supersaturated state causing nucleation and subsequent growth of crystals comprising constituents of the solution. It should be appreciated that the functional groups act as an antisolvent in the solution, wherein when added to a solution such that the solution becomes supersaturated they reduce the solution solubility. In some embodiments, a "saturated solution" refers to a solution comprising solute and solvent, wherein if any more solute is added (e.g., at a particular temperature), then the additional solute will not dissolve in the solution. This is referred to as the solution saturation point, wherein the solute and solvent of a saturated solution are at equilibrium. Under certain conditions equilibrium solubility or saturation point may be exceeded to give a so-called "supersaturated solution", which is also referred to as a metastable zone. In some embodiments, a Metastable Zone Width (MSZW) is the difference between the saturation temperature and the temperature at which crystals are detected under constant cooling rate.

In some embodiments, a supersaturated solution can be obtained by adding more solute to a solution comprising the solute, wherein the solution is at saturation or before adding the more solute. An "undersaturated solution" refers to a solution that is below the saturation point of the solution (below saturation) for a particular solute. In some embodiments, the solution comprises a compound of interest. In some embodiments, the solution comprises a solute which comprises the compound of interest. In some embodiments, the solution comprises impurities. In some embodiments, impurities comprise unwanted solids, chemicals, and/or particulates of the impure solution. In some embodiments, impurities comprised in the solution can be crystallized by an effective amount of functionalized nanoparticles. In some embodiments, an effective amount refers to an amount of functionalized nanoparticles that can induce crystallization of impurities comprised in the impure solution. In some embodiments, impurities comprised in the solution can be filtered.

In some embodiments, a saturated solution is made by the methods described herein. In some embodiments, a saturated solution containing functionalized nanoparticles is mixed, stirred, or agitated to produce a slurry of crystals comprising the compound of interest. In some embodiments, the crystals are recovered. In some embodiments, the crystals are recovered by centrifugation or filtration. In some embodiments, a magnet is useful when using magnetic nanoparticles in the crystallization techniques of the disclosure. In some embodiments, after adding magnetic functionalized nanoparticles to the solution, crystallization occurs. In some embodiments, a magnet is used to separate the magnetic nanoparticles from the crystals and solution and the crystals are recovered by filtration or centrifugation.

In some embodiments, crystallization from a supersaturated solution involves a two-step process of nucleation and crystal growth. In some embodiments, nucleation involves the creation or "birth" of new crystals (nuclei). In certain embodiments, once created, these nuclei can grow to larger sizes during a growth step, in which particles are transported (e.g. by convection and/or diffusion) to the surface of the nuclei to be incorporated into a crystal lattice. In some embodiments, the nucleation is primary nucleation wherein the nanoparticle does not provide a nucleation site for crystallization, but rather the primary nucleation occurs in the supersaturated solution, which is a novel finding of the present disclosure and an important distinction from what is known in the art. In other words, in embodiments of the disclosure, primary nucleation occurs in bulk in the supersaturated solution that is created by the nanoparticles that cause supersaturation, not on the nanoparticles and not on a solid surface.

In some embodiments, nucleation may be classified as primary nucleation. In some embodiments, primary nucleation occurs in the absence of crystalline surfaces. In some embodiments, nucleation may involve solute molecules combining in a series of bi-molecular reactions to produce ordered aggregates. However, in some embodiments, nucleation may involve formation of sufficient-sized clusters of solute molecules, followed by reorganization of the clusters into ordered structures. In some embodiments, primary nucleation mechanisms are advantageous in precipitation processes and for crystallization in regions of high local supersaturation.

In some embodiments, a functional group that reduces solution solubility is referred to as a "solubility-lowering agent". Functional groups or solubility-lowering agents of the disclosure, without limitation, include thiols, carboxyl groups, hydroxyl groups, and ethyl acetate. Other functional groups may be used. In some embodiments, functionalized nanoparticles of the disclosure are surface-coated with a functional group or solubility-lowering agent. Surface-coated nanoparticles are nanoparticles that comprise functional groups attached (e.g., through covalent or non-covalent bonds) to the surface of the nanoparticle. However, in some embodiments, functional groups may be used that increase solution solubility (e.g., with respect to a particular solute). In such embodiments, the functional group may be referred to as a "solubility-increasing agent."

In some embodiments, nanoparticles are small enough, such that the functionalized nanoparticles may be added to a solution in an effective amount to allow reduction of solubility to cause crystallization. In some embodiments, when added to the solution, the functional groups or solubility-lowering agents of the functionalized nanoparticles cover enough surface area within the solution to comprise an effective amount. In some embodiments, the functional group or solubility-lowering agent comprises a thiol, a carboxyl, or a hydroxyl group.

In some embodiments, the functional group remains bound or attached to the nanoparticle when present in the solution. In some embodiments, a solubility-lowering agent is a functional group that remains attached to the nanoparticle when present in the solution. In some embodiments, functional groups of the disclosure can comprise a tail group attached to the surface of a nanoparticle, e.g., thiols can functionalize a tail group on gold and hydroxyl groups can functionalize a tail group on silicon dioxide. Examples of bonding motifs between nanoparticles and functional groups are show in FIGS. 3A and 3B. In some embodiments, the functional groups attached to the functionalized nanoparticles may act as an antisolvent in the solution. Calculations of amounts of functionalized nanoparticles needed to induce crystallization are provided in the examples.

In some embodiments, the nanoparticle is functionalized with a self-assembled monolayer (SAMs). The self-assembled monolayer (SAM) can comprise a multitude of solvation-affecting chemical groups. The solvation-affecting chemical groups can be hydrophilic groups, hydrophobic groups, or combinations thereof. In certain embodiment, the SAM comprises hydrophobic groups, such as unsubstituted aliphatic groups (e.g., unsubstituted, branched or unbranched alkyl groups; unsubstituted, branched or unbranched alkenyl groups; unsubstituted, branched or unbranched alkynyl groups; fluorine-substituted alkyl groups). In certain embodiments, the SAM comprises hydrophilic groups, such as substituted aliphatic groups (e.g., substituted alkyl groups). As described herein, hydrophilic moieties are moieties comprising hydrogen bond donors groups and/or hydrogen bond acceptor groups (e.g., hydroxyl, amino, thio, sulfonate, sulfinate, carbonyl, phosphate, oxo groups, charged groups, and other substituents described herein).

"Hydrophobic" or "lipophilic" refers to the ability of a compound to dissolve—or the ability of a moiety of a compound to assist the compound in dissolving—in fats, oils, lipids, and/or non-polar solvents. Hydrophobic compounds or moieties typically have a relatively high octanol/water partition coefficient. In certain embodiments, hydrophobic moieties are substituted or unsubstituted, branched or unbranched, aliphatic groups. The term "aliphatic" refers to alkyl, alkenyl, alkynyl, and carbocyclyl groups, and combinations thereof.

"Hydrophilic" refers to the ability of a compound or moiety to mix with or dissolve in water or other polar solvents. It may also refer to the ability of a group on a compound to assist the compound in mixing or dissolving with water or other polar solvents. Typically, hydrophilic compounds or moieties typically have a relatively low octanol/water partition coefficient. Hydrophilic moieties comprise one or more hydrogen bond donor groups and/or one or more hydrogen-bond acceptor groups. Hydrogen bond donor and acceptor groups are typically heteroatom-containing groups (e.g., hydroxyl, amino, thio, sulfonate, sulfinate, carbonyl, phosphate, oxo groups). In certain embodiments, hydrophilic moieties are substituted, branched or unbranched, aliphatic groups. In certain embodiments, hydrophilic moieties are substituted, branched or unbranched alkyl groups.

The self-assembled monolayer (SAM) of a particle can be assembled by associating a multitude of small molecules (i.e., ligands) to the outer sphere of the particle. As described herein, the molecules comprising the SAM mimic solvent molecules and modulate the solubility of other components of a mixture. The molecules can be bound to the nanoparticle via covalent or non-covalent bonding. For example, when the particle is a metallic particle, the molecules may be ligands that are non-covalently bound to the nanoparticle via chelation.

For example, in certain embodiments, the small molecule ligands forming the SAM have sulfur, nitrogen, or oxygen-containing groups capable of associating with the outer sphere of the metallic nanoparticle. For instance, in certain embodiments, the small molecule ligands comprise —SH, —NH$_2$, —OH, or —CO$_2$H groups.

In some embodiments, the SAMs include a thiol and/or silane based surfactant molecule. In some embodiments, the SAM is comprised of molecules of the formula HO-alkyl-X, HS-alkyl-X, H$_2$N-alkyl-X, HO$_2$C-alkyl-X, R$_3$Si-alkyl-X, or (RO)$_3$Si-alkyl-X, or combinations thereof; wherein X and R are as defined herein. In some embodiments, the SAM is comprised of molecules of the formula HS-alkyl-X. In some embodiments, the SAM is comprised of molecules selected from: short and long chain alkanethiols of the formula SH(CH$_2$)$_n$X; where n represents chain length, wherein n may be 1, 2, 3, 4, 5, 6, 7, 8, 9, 10 or more and X represents an organic or inorganic functional tail group. In some embodiments, the SAM is comprised of molecules of the formula HO$_2$C-alkyl-X. In some embodiments, the SAM is comprised of molecules of the formula HO$_2$C(CH$_2$)$_n$X, where n represents chain length, wherein n may be 1, 2, 3, 4, 5, 6, 7, 8, 9, 10 or more and X represents an organic or inorganic functional tail group. In certain embodiments, the SAM is comprised of aromatic thiolates optionally comprising X group(s). In some embodiments, the SAM is comprised of molecules of the formula (RO)$_3$Si-alkyl-X. In some embodiments, the SAM is comprised of molecules of the formula (RO)$_3$Si(CH$_2$)$_n$X. In some embodiments, the SAM is comprised of molecules of the formula (CH$_3$CH$_2$O)$_3$Si-alkyl-X. In some embodiments, the SAM is comprised of molecules of the formula (CH$_3$CH$_2$O)$_3$Si(CH$_2$)$_n$X. In some embodiments, the SAM is comprised of molecules of the formula (CH$_3$O)$_3$Si-alkyl-X. In some embodiments, the SAM is comprised of molecules of the formula (CH$_3$O)$_3$Si(CH$_2$)$_n$X.

In certain embodiments, the functional group tail X is selected from the group consisting of —CN, —NO$_2$, —N$_3$, —SO$_2$H, —SO$_3$H, —OH, —OR, —ON(R)$_2$, —N(R)$_2$, —N(R)$_3$$^+$Y$^-$, —N(OR)R, —SH, —SR, —SSR, —C(=O)R, —CO$_2$H, —CHO, —C(OR)$_2$, —CO$_2$R, —OC(=O)R, —OCO$_2$R, —C(=O)N(R)$_2$, —OC(=O)N(R)$_2$, —NRC(=O)R, —NRCO$_2$R, —NRC(=O)N(R)$_2$, —C(=NR)R, —C(=NR)OR, —OC(=NR)R, —OC(=NR)OR, —C(=NR)N(R)$_2$, —OC(=NR)N(R)$_2$, —NRC(=NR)N(R)$_2$, —C(=O)NRSO$_2$R, —NRSO$_2$R, —SO$_2$N(R)$_2$, —SO$_2$R, —SO$_2$OR, —OSO$_2$R, —S(=O)R, —OS(=O)R, —Si(R)$_3$, —OSi(R)$_3$—C(=S)N(R)$_2$, —C(=O)SR, —C(=S)SR, —SC(=S)SR, —SC(=O)SR, —OC(=O)SR, —SC(=O)OR, —SC(=O)R, —P(=O)(R)$_2$, —P(=O)(OR)$_2$, —OP(=O)(R)$_2$, —OP(=O)(OR)$_2$, —P(=O)(N(R)$_2$)$_2$, —OP(=O)(N(R)$_2$)$_2$, —NRP(=O)(R)$_2$, —NRP(=O)(OR)$_2$, —NRP(=O)(N(R)$_2$)$_2$, —P(R)$_2$, —P(OR)$_2$, —P(R)$_3$$^+$Y$^-$, —P(OR)$_3$$^+$Y$^-$, —P(R)$_4$, —P(OR)$_4$, —OP(R)$_2$, —OP(R)$_3$$^+$Y$^-$, —OP(OR)$_2$, —OP(OR)$_3$$^+$Y$^-$, —OP(R)$_4$, —OP(OR)$_4$, —B(R)$_2$, —B(OR)$_2$, and —BR(OR); wherein each instance of R is independently hydrogen, alkyl, alkenyl, alkynyl, aryl, heteroaryl, carbocyclyl, heterocyclyl, acyl, or a protecting group; and wherein Y is a counterion. In some embodiments, the functional tail group (X) is selected from: —CO$_2$$^-$, —SO$_3$$^-$, —PO$_3$$^-$, —NH$_3$$^+$, —N(CH$_3$)$_3$$^+$, —NO$_2$, —OH, —CH$_3$, —CF$_3$, —F, —Cl, —Br, —I, —CO$_2$CH$_3$, —SH, —C$_2$H$_4$OH and —SCH$_3$. In certain embodiments, X is —OR. In certain embodiments, X is —OH.

In certain embodiments, the SAM is comprised of ligands of the formula HS—CH$_2$CH$_2$—OH (i.e., 2-mercaptoethanol). In certain embodiments, the SAM is comprised of ligands of the formula HO$_2$C—CH$_2$CH$_2$—OH. In certain embodiments, the SAM is comprised of ligands of the formula HO—CH$_2$CH$_2$—OH. In certain embodiments, the SAM is comprised of ligands of the formula HN—CH$_2$CH$_2$—OH. In certain embodiments, the SAM may comprise polymeric ligands (e.g., polyethylene glycol (PEG)-containing ligands such as HS-PEG, HS-PEG-X, HS-PEG-OH, HO-PEG, HO-PEG-X, HO-PEG-OH, H$_2$N-PEG, H$_2$N-PEG-X, H$_2$N-PEG-OH, HO$_2$C-PEG, HO$_2$C-PEG-X, HO$_2$C-PEG-OH, R$_3$Si-PEG, R$_3$Si-PEG-X, (RO)$_3$Si-PEG, (RO)$_3$Si-PEG-X, etc.). Other small molecule ligands capable of self-assembling into a monolayer on the surface of a particle and comprising solvation-affecting chemical groups are disclosed herein. Further examples of nanoparticles with self-assembled monolayers can be found in the literature; see, e.g., Rotello et al. *Adv Drug Deliv Review.* 2012 64, 200-216; Mirkin et al. *Angew Chem Int Ed Engl* 2010, 49, 3280-3294; Singh et al. *Nanomaterials* 2011, 1, 31-63; Irvine et al. *Nature Materials* 2008, 7, 588-595; Irvine et al. *Nano Letters* 2013, 13, 4060-4067; and references cited therein, all of which are incorporated herein by reference.

In certain embodiments, the self-assembled monolayer (SAM) of the particle comprises one or more reactive groups. In certain embodiments, the small molecule ligands forming the SAM are functionalized with one or more reactive group, thereby installing the reactive groups on the surface of the particle. The reactive groups can be used in chemical ligation to a substrate, e.g., for sequestration and/or removal of the particle from the medium. In certain embodiments, the reactive groups have particular affinity for a substrate; and affinity chromatography can be used to capture the particle. In certain embodiments, for example, the reactive groups are click chemistry handles; and click chemistry may be used to capture the particle. In certain embodiments, the reactive group is biotin. When the reactive group is biotin, biotinylation can be used to capture the particle. In certain embodiments, the biotin-avidin interaction can be used to capture the particle.

The particles can be captured via click chemistry by reaction of one or more click chemistry handles on the SAM of the particle. "Click chemistry" refers to a chemical approach to conjugation introduced by Sharpless in 2001 and describes chemistry tailored to generate substances quickly and reliably by joining units together. See, e.g., Kolb, Finn and Sharpless *Angewandte Chemie International Edition* 2001 40, 2004-2021; Evans, *Australian Journal of Chemistry* 2007 60, 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition reactions); and Diels-Alder reactions (e.g., tetrazine [4+2] cycloaddition). Examples of click chemistry reactions can be found in, e.g., Kolb, H. C.; Finn, M. G. and Sharpless, K. B. *Angew. Chem. Int. Ed.* 2001, 40, 2004-2021. Kolb, H. C. and Sharless, K. B. *Drug Disc. Today,* 2003, 8, 112-1137; Rostovtsev, V. V.; Green L. G.; Fokin, V. V. and Shrapless, K. B. *Angew. Chem. Int. Ed.* 2002, 41, 2596-2599; Tomoe, C. W.; Christensen, C. and Meldal, M. *J. Org. Chem.* 2002, 67, 3057-3064. Wang, Q. et al. *J. Am. Chem. Soc.* 2003, 125, 3192-3193; Lee, L. V. et al. *J. Am. Chem. Soc.* 2003 125, 9588-9589; Lewis, W. G. et al. *Angew. Chem. Int. Ed.* 2002, 41, 1053-41057;

Manetsch, R. et al., *J. Am. Chem. Soc.* 2004, 126, 12809-12818; Mocharla, V. P. et al. *Angew. Chem., Int. Ed.* 2005, 44, 116-120.

In some embodiments, an effective amount of nanoparticles is added to a solution. An effective amount refers to an amount of functionalized nanoparticles that can induce nucleation and subsequent crystallization of a compound or of impurities comprised in the solution. In some embodiments, an effective amount refers to the amount of functionalized nanoparticles that can induce an increase in the solubility of a compound/solute (solubilization) contained in a solution or slurry. In some embodiments, an effective amount refers to the amount of functionalized nanoparticles that can induce an increase in the solubility of a compound/solute. In some embodiments, an effective amount can be defined as the amount of functionalized nanoparticles needed to be added to a solution to cause crystallization of the compound of interest. In some embodiments, the effective amount may be measured in terms of density of the functionalized nanoparticles within the solution. Theoretical and example calculations are provided in Tables 2-7 and described within the Examples. In some embodiments, an effective amount of functionalized nanoparticles in the solution will cause the solution to transform to a supersaturated state in which primary nucleation and subsequent growth of crystals comprising the compound of interest occurs.

In some embodiments, the nanoparticle comprises glass, including controlled pore glass. In some embodiments, the nanoparticle comprises plastic. In some embodiments, the nanoparticle comprises a metal. In some embodiments, the metal is selected from: aluminum, beryllium, bismuth, cadmium, carbon, cobalt, copper, germanium, gold, hafnium, indium, iridium, iron, lead, magnesium, molybdenum, nickel, niobium, palladium, platinum, rhenium, rhodium, silicon, silver, tantalum, tin, titanium, tungsten, vanadium, zinc, and zirconium. In some embodiments, the metal is any metal that can have its surface functionalized. In some embodiments, the metal is in a substantially pure form. In some embodiments, the metal is in the form of a metal oxide. In some embodiments, the metal oxide is a silver oxide, iron oxide, or silicon dioxide. In some embodiments, the metal is gold. In some embodiments, the nanoparticle is magnetic.

Figure 28:
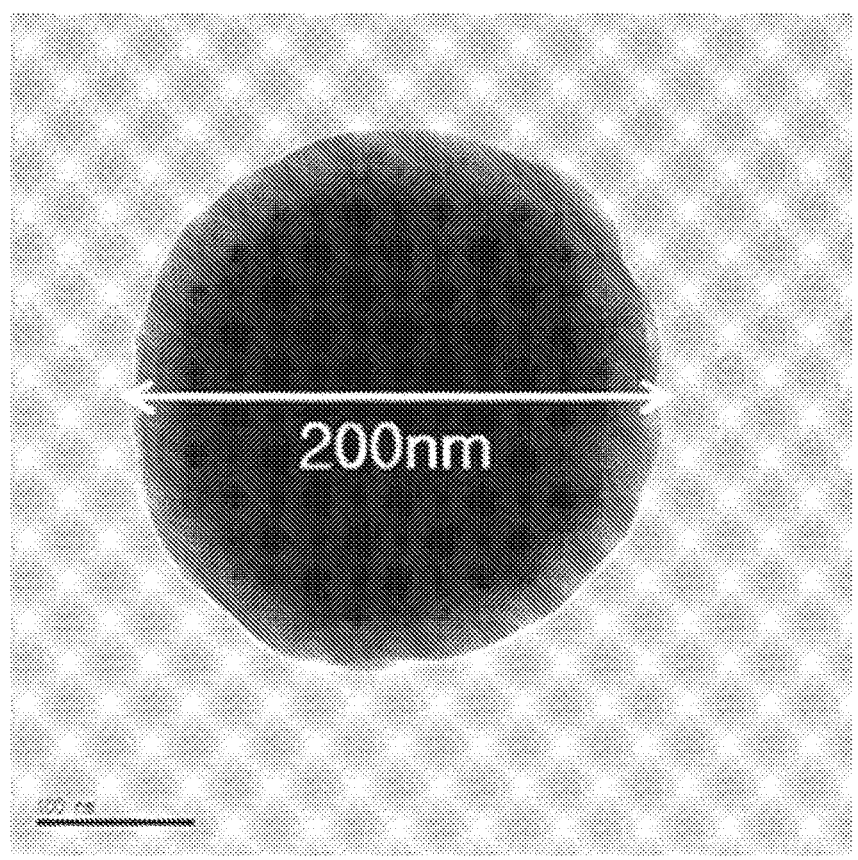
FIG. 28 is an image of a silica coated iron oxide nanoparticle.

In some embodiments, the nanoparticles are core shell nanoparticles. In some embodiments, the core shell nanoparticle is a multi-shell nanoparticle. In some embodiments, the core shell nanoparticle is a solid shell nanoparticle. In some embodiments, the core shell nanoparticle is a porous shell nanoparticle. In some embodiments, the core shell nanoparticle is a hollow nanoparticle. In some embodiments, the core of the nanoparticle comprises glass, including controlled pore glass. In some embodiments, the core of the nanoparticle comprises plastic. In some embodiments, the core of the nanoparticle comprises any of the metals described herein. In some embodiments, the core of the nanoparticle comprises silver oxide, iron oxide, or silicon dioxide. In some embodiments, the core of the nanoparticle is gold. In some embodiments, the shell of the nanoparticle comprises glass, including controlled pore glass. In some embodiments, the shell of the nanoparticle comprises plastic. In some embodiments, the shell of the nanoparticle comprises any of the metals described herein. In some embodiments, the shell of the nanoparticle is silica. An exemplary silica coated iron oxide nanoparticle is shown in FIG. 28.

In some embodiments, the nanoparticle is spherical. In some embodiments, the nanoparticle is approximately spherical. In some embodiments, the nanoparticle is of a non-spherical shape. In some embodiments, the size of the nanoparticle, regardless of shape, can be measured. In some embodiments, the nanoparticle is measured by diameter, wherein the nanoparticle is spherical or essentially spherical in shape. In some embodiments, the nanoparticle is measured in "average diameter" or "Feret diameter", wherein the nanoparticle is not spherical in shape or wherein the nanoparticle is not essentially spherical in shape. In embodiments in which the nanoparticle is not spherical, the size of the nanoparticle can be measured in average diameter ("Feret diameter"). In some embodiments in which the nanoparticle is not essentially spherical, the size of the nanoparticle can be measured in average diameter. In some embodiments, the nanoparticle is less than 10 nm in diameter, average diameter, or Feret diameter. In some embodiments, the nanoparticle is approximately 1 nm to 10 nm, e.g., 1, 1.1, 1.2, 1.3, 1.4, 1.5, 1.6, 1.7, 1.8, 1.9, 2, 3, 4, 5, 6, 7, 8, 9, or 10 nm in diameter, average diameter, or Feret diameter in size.

In some embodiments, the surface area per nanoparticle in the solution is approximately $4 \pi r^2$, wherein "r" denotes radius. As used herein, radius can be calculated as one-half of diameter. As used herein, average radius can be calculated as one-half of a Feret diameter. A "Feret diameter" is the distance between the two parallel planes or lines that are tangential to an object (e.g., nanoparticle or crystal). In some embodiments, the measure may be applied to projections of a three-dimensional object on a two-dimensional (2D) plane. In such cases, the Feret diameter is the distance between two tangential parallel lines rather than planes. This measure may be used in the analysis of particle sizes, for example, in microscopy. A mean Feret diameter of an object (e.g., nanoparticle) is the mean of a plurality of distances (e.g., 2, 3, 4, 5, 6, 7, 8, 9, 10, 100, 1000 or more distances), in which each distance in the plurality is the distance between two different parallel planes or parallel lines that are tangential to the object or projection of the object on a 2D plane.

In some embodiments, a measurement indicative of the physical dimension of the object, e.g., nanoparticle, may be a measure of size and/or shape in two or three dimensions. For example, the measurement may be a Feret diameter (e.g., average Feret diameter), a cross-sectional diameter, an equivalent circle diameter, an equivalent sphere diameter, a convex hull perimeter, circularity, convexity, extent of elongation, etc. The summary statistic may be mean, median, mode, standard deviation, variance, coefficient of variation, skewness, kurtosis, D10, D90 percentiles, and so on. Any of appropriate summary statistics may serve as a characteristic size of a population.

In some embodiments, the surface area of functionalized nanoparticles in the solution is in the range of 1 nm nanoparticles/ml solution to 100 nm nanoparticles/ml solution, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nm nanoparticles/ml solution. In some embodiments, the density of nanoparticles in the solution is approximately 0.1 g nanoparticle/ml to 30 g nanoparticles/ml solution density of nanoparticles in the solution is approximately 0.1 g nanoparticle/ml solution to 30 g nanoparticles/ml solution, e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 18.1, 18.2, 18.3, 18.4, 18.5, 18.6, 18.7, 18.8, 18.9, 19, 19.1, 19.11, 19.12, 19.13, 19.14, 19.15, 19.16, 19.17, 19.18, 19.19, 19.2, 19.21, 19.22, 19.23, 19.24, 19.25, 19.26, 19.27, 19.28, 19.29, 19.3, 19.31, 19.32, 19.33, 19.34, 19.35, 19.36, 19.37, 19.38, 19.39, 19.4, 19.41, 19.42, 19.43, 19.44, 19.45, 19.46, 19.47, 19.48, 19.49, 19.5, 19.51, 19.52, 19.53, 19.54, 19.55, 19.56, 19.57, 19.58, 19.59, 19.6, 19.7, 19.8, 19.9, 20, 21, 22, 23, 24, 25, 26, 27, 28, 29, or 30 g nanoparticles per ml solution. In some embodiments, the density of nanoparticles in the solution is approximately 19.32 g nanoparticles/ml solution.

In some embodiments, the density of the functional groups on the nanoparticle is such that the solubility of the solute is changed by 1.1×, 1.2×, 1.3×, 1.4×, 1.5×, 1.6×, 0.7×, 1.8×, 1.9×, 2.0×, 2.5×, 3.0×, 4.0×, 5.0×, 10.0× or more. In some embodiments, the density of the functional groups on the nanoparticle is such that the solubility of the solute is changed by 1, 2, 3, 4, 5, 10, 20, 50, 100, 150, 200, 300, 400, 500 mM or more.

In some embodiments, templates or organized substrates may be used to facilitate the formation and orientation of critical nuclei from supersaturated solution. In some embodiments, template reduces the activation energy of nucleation by providing the heterogeneous sites, therefore reducing the energy barrier needed for heterogeneous nucleation of certain polymorphs. In some embodiments, heterogeneous nucleation is the type of primary nucleation for which the nuclei are formed at heterogeneous nucleation centers (dust particles, glass wall, stirrer etc). In some embodiments, well-defined templates are used to control crystal morphology, crystal polymorph and crystal size. In some embodiments, self-assembled monolayers (SAMs) may be used to control nucleation and growth of crystals during crystallization. In some embodiments, SAMs are well-assembled molecules with a head group bound to a substrate, a chain or backbone and the free end group pointing outwards. In some embodiments, a wide range of end groups can act as templates for nucleation and crystal growth by providing a surface to nucleate and orienting the growth of crystals. Polymorphic control can be achieved in some cases by using well-defined templates (heterogeneous nucleation). In some embodiments, a large variety of well-defined templates (self-assembled monolayers) are used as nucleation sites to produce specific design of crystals. In some embodiments, SAMs of functionalized nanoparticles are used in place of an antisolvent for purposes of crystallization of a compound of interest.

In some embodiments, gold nanoparticles (GNP's) functionalized with thiol containing molecules forming self-assembling monolayers are often used as a heterogeneous surface to crystallize chemical and pharmaceutical compounds. In the present disclosure, functionalized nanoparticles may be used to crystallize organic and inorganic compounds from undersaturated solutions similarly as antisolvent crystallization. In some embodiments, the extent of surface coverage of functionalized nanoparticles is important to accurately determine the amount of nanoparticles that may be used to replace the volume of antisolvent. In some embodiments, in the present disclosure, nucleation, e.g., primary nucleation, does not occur on a surface, but rather occurs in the solution that is a supersaturated solution.

In some embodiments, a compound comprised in a solution, the compound of interest, is any organic compound or any inorganic compound. In some embodiments, the compound of interest is an organic compound. In some embodiments, the compound of interest is an inorganic compound. In some embodiments, the compound of interest comprises a small molecule, an active pharmaceutical ingredient (API), a salt, or a macromolecule, e.g., a protein or nucleic acid. In some embodiments, the compound of interest comprises a protein.

It will be appreciated that the solutions described herein can comprise different solvents. Appropriate solvents include, for example, heptane, tert-Butyl methyl ether (TBME), diethyl ether (DEE), butyl acetate, ethyl acetate, isobutylacetate, anisole, isopropylacetate, propylace, methylisobutylket, pentane, methylace, methylethylket, ethyl formate, acetone, 2-butanol, 2-propanol, 3-methyl-1-butanol, 1-pentanol, 2-methylpropanol, 1-butanol, 1-propanol, ethanol, and water.

In some embodiments, the nanoparticles are separated from the solution by a magnet. In some embodiments, the magnet is applied to the side of a vessel housing the solution. In some embodiments, the magnet is inserted into the solution to collect the nanoparticles, for example, as a dipstick.

In some embodiments, the strength of the magnet is 1-500 mT. In some embodiments, the strength of the magnet is at least 1, 5, 10, 15, 20, 25, 30, 40, 50, 60, 70, 80, 90, 100, 110, 120, 130, 140, 150, 160, 170, 180, 190, 200, 250, 300, 350, 400, 450, or 500 mT. In some embodiments, the strength of the magnet is in a range of 5 mT-100 mT, 5 mT-50 mT, 20 mT-100 mT, 50 mT-150 mT, 50 mT-200 mT, or 100 mT-500 mT.

In some embodiments, the nanoparticles are separated from the solution by centrifugation. In some embodiments, the nanoparticles are separated from the solution by filtration. In some embodiments, the nanoparticles are separated from the solution by affinity purification. For example, in some embodiments, the nanoparticle comprises biotin and the nanoparticle is separated from the solution by being contacted with streptavidin. In some embodiments, the nanoparticle comprises a carbohydrate or an amino acid.

In some embodiments, the nanoparticles are separated from the solution by a membrane. Suitable types of membrane include, for example, a nanofiltration membrane or a reverse osmosis membrane. In such embodiments, the solution can be separated from the nanoparticles by flow of the solution through the membrane, leaving the nanoparticles confined on the other side of the membrane. In some embodiments, a solute is passed through the reaction vessel membrane by reverse osmosis.

In some embodiments, the crystals comprising the compound of interest are separated from the solution. In some embodiments, the crystals comprising the compound of interest are separated from the solution by centrifugation. In some embodiments, crystals comprising the compound of interest are separated from the solution by filtration.

In some embodiments, the process of adding nanoparticles to a solution to supersaturate the solution and produce crystals is followed by removal of the nanoparticles and dissolution of the crystals, and this process is repeated one or more times to control the size of the crystals. This occurs because while all of the crystals present will dissolve to some degree when the solubility is increased, the smallest crystals will completely dissolve. During the growth phase, when the solubility has declined, existing crystals grow but the supersaturation driving force is insufficient for new crystal nucleation thus increasing the crystal size distribution (CSD). This process is known as aging or ripening.

In some embodiments, a first population of nanoparticles having a first type of functional group and a second population of nanoparticles having a second type of functional group are both added to the same solution. In some embodiments, the first and second types of functional groups are solubility-lowering agents. In some embodiments, the first and second types of functional groups are solubility-increasing agents. In this situation, the solution generated can resemble a ternary solvent system which can be used to manipulate solvent properties and chemical reaction rates.

In some embodiments, the nanoparticles are housed in a reaction vessel. In some embodiments, the reaction vessel comprises a bottle, tube, or flask. In some embodiments, the reaction vessel comprises a container. In some embodiments, the reaction vessel comprises a column. In some embodiments, the reaction vessel comprises a reactor.

In some embodiments, the reaction vessel comprises a reactor. In some embodiments, a reactor is a continuous stir tank reactor. In some embodiments, a reactor is a continuous flow stir tank reactor. In some embodiments, reagents flow into the reactor and reactants flow out of the reactor. In some embodiments, the mass of the reagents entering the reactor approximately equals the mass of the reactants exiting the reactor. In some embodiments, the volume of the reagents entering the reactor approximately equals the volume of the reactants exiting the reactor. In some embodiments, the reactor is a reactor for the production of an API.

In some embodiments, the reactor comprises a solution that is mixed or agitated.

In some embodiments, the reactor comprises a magnet at or near the outflow where the reactants leave the tank. In such embodiments, the nanoparticles can be collected from the reactor solution as the product leaves the tank via the magnet.

In some embodiments, the reaction vessel comprises a batch crystallizer for the production of crystals. Batch crystallizers generally produce a supersaturated state by (i) cooling; (ii) evaporation; (iii) vacuum; (iv) dilution; or (v) reaction. In some embodiments, the reaction vessel comprises a batch crystallizer in which a supersaturated state of a solution in the crystallizer is achieved by addition of the nanoparticles described herein. In some embodiments, the solution in the batch crystallizer is mixed or agitated.

In some embodiments, the reaction vessel comprises a syringe comprising, e.g., an injectable therapeutic for injection into a subject. In some embodiments, nanoparticles in the syringe function to increase the solubility of an API prior to injection. This is particularly useful in the context of low-solubility APIs such as taxanes. Taxanes are currently formulated in micellular solutions that can cause allergic reactions. In some embodiments, the solution comprising the API comprises 0.1%, 1%, 2%, 3%, 4%, 5%, 10%, 15%, or 20% up to 50% wt/wt nanoparticles. In some embodiments, the nanoparticles are removed from the solution by filtration within the syringe prior to injection. In some embodiments, the nanoparticles are removed from the solution by filtration within the syringe as the solution is being injected. In some embodiments, the nanoparticles are filtered such that less than 1%, 0.5%, 0.1%, 0.05%, 0.01%, 0.005% or 0.001% of the nanoparticles are injected into the subject.

In some embodiments, the contents of the reaction vessel are mixed by vortexing, by agitation, by using a magnetic stirrer, by using a mechanical stirrer, by otherwise stirring, or by blending.

In some embodiments, the properties of the solution are measured. Properties that are measured include, for example, optical density, purity, osmolarity, pH, infrared spectra, conductivity, etc. In some embodiments, the properties of the solution are measured after removal of the nanoparticles. In some embodiments, the nanoparticles are temporarily removed from solution so that the properties can be measured and the nanoparticles are then returned to the solution. This can be accomplished, for example, by applying the charge of a magnet, e.g., an electromagnet, to the solution containing the nanoparticles while the solution is sampled. In some embodiments, the electromagnet is applied to the wall of a reaction vessel housing the nanoparticles. In some embodiments, the electromagnet is activated or contacted to the reaction vessel for 60 seconds or less, 50 seconds or less, 40 seconds or less, 30 seconds or less, 20 seconds or less 10 seconds or less, 10 seconds or less or 5 seconds or less. In some embodiments, a computer program controls the activation and deactivation of the magnet based on the properties of the solution.

In some embodiments, the properties of the solution are measured while the nanoparticles are in the solution. In some embodiments, the size distribution of the crystals can be measured with a probe. In some embodiments, the probe is a laser back scattering inline device probe (e.g., a Lasentec® probe).

Other aspects of the disclosure provide for a method for purifying an impure solution. In some embodiments, a system is provided for producing the same. For example, we can purify water from impurities or purify an active pharmaceutical ingredient (API) from its impurities (see Examples 2 and 3, respectively) using methods and systems described herein. In some embodiments, the purified compound, e.g. API, is crystallized outside of the column. A column of the present disclosure can comprise an effective amount of functionalized nanoparticles that can crystallize impurities comprised in a solution. A column of the present disclosure can range in size from 5 cm to 10 m for batch and continuous purification processes. A column of the present disclosure may comprise a membrane comprising a pore size of 10-50 m with a filtration cut off of 2 nm particles.

Impure solutions of the disclosure can be up to 50 percent impure, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 percent impure.

Other aspects of the disclosure provide for methods for desalinating water. For example, in some embodiments, the nanoparticles described herein can be used to reduce the salt concentration in the highly saline water produced by water treatment plants. In some embodiments, the nanoparticles are added to the highly saline water to produce a supersaturated solution. In some embodiments, addition of the nanoparticles to the highly saline water results in formation of salt crystals. In some embodiments, the salt crystals formed are separated from the solution. The desalinated water can then be disposed of without environmental concerns. In some embodiments, the nanoparticles are retrieved from the desalinated water, e.g., before disposal.

Other aspects of the disclosure provide for methods for altering a reaction rate. In some embodiments, the methods comprise adding the nanoparticles of the invention to a solution in which a chemical reaction is occurring or will occur. In some embodiments, the addition of the nanoparticles increases the rate of the chemical reaction. The nanoparticles can increase the rate of the chemical reaction by, for example, increasing the solubility of a reactant in the solution. If that reactant is rate limiting, the reaction will proceed at a faster rate if the solubility of that reactant is increased, such that more of the reactant is available for the chemical reaction. In some embodiments, the solubility of a reactant is increased 5%, 10%, 20%, 30%, 40%, 50%, 60%, 70%, 80%, 90%, 100%, 200%, 300%, 400%, or 500% or more. The nanoparticles can also increase the rate of the chemical reaction by, for example, decreasing the solubility of a product in the solution. By precipitating the product out of solution and decreasing the concentration of the product in solution, the equilibrium of the reaction can be shifted towards the product. In some embodiments, the solubility of the product is decreased 5%, 10%, 20%, 30%, 40%, 50%, 60%, 70%, 80%, 90%, 100%, 200%, 300%, 400%, or 500% or more. The nanoparticles can also increase the rate of the chemical reaction by, for example, solubilizing a catalyst. In some embodiments, the addition of the nanoparticles decreases the rate of the chemical reaction.

Other aspects of the disclosure provide for methods for gas hydrate inhibition. Natural gas hydrates are solid hydrogen-bonded water crystals containing small molecular gases. Hydrate blockages hinder oil/gas pipeline transportation. Accordingly, hydrate inhibition has the potential to be highly beneficial in practical applications such as hydrate exploitation, oil/gas transportation, and flow assurance. Methanol can be used to inhibit gas hydrate formation by reducing the solubility of the gas. Similarly, in some embodiments, nanoparticles can be added to areas of gas hydrate formation to reduce the solubility of the gas. In some embodiments, the nanoparticles are functionalized with methanol-like groups.

Provided herein are kits comprising the functionalized nanoparticles described herein.

In one aspect, provided herein is a kit for forming crystals or increasing the solubility of a solute using the nanoparticles described herein. In some embodiments, the kit comprises a container comprising the functionalized nanoparticles. In some embodiments, the kit comprises a reaction vessel for formation of the crystals. In some embodiments, the kit comprises a magnet for retrieving the functionalized nanoparticles. In some embodiments, the magnet is designed such that it is applied to the side of the reaction vessel. In some embodiments, the magnet is designed such that it is dipped into the reaction vessel.

In another aspect, provided herein is a kit for crystallizing protein using the nanoparticles described herein. Protein crystallization is done in small drops. In some embodiments, the kit comprises a container comprising the functionalized nanoparticles. In some embodiments, the kit comprises a buffer for protein crystallization. In some embodiments, the kit comprises a petri-dish, a microtiter plate, a test tube, or any other small volume reaction vessel for performing the protein crystallization reaction. In some embodiments, the reaction vessel is pre-loaded with the appropriate volume of nanoparticles. In some embodiments, the kit comprises a magnet for applying to the exterior of the reaction vessel for retrieval of the nanoparticles.

In another aspect, provided herein is a kit for purifying an impure solution, for example, for purifying impurities from water, or for purifying an active pharmaceutical ingredient (API) from its impurities (see Examples 2 and 3, respectively). In some embodiments, the kit comprises a column pre-loaded with nanoparticles, as is described herein. In some embodiments, the column is in an automated system in which the impure solution is continuously added to the system. In some embodiments, the kit comprises buffers for equilibrating the column before use.

In another aspect, provided herein is a kit for injecting an insoluble API into a subject. In some embodiments, the kit comprises a container comprising the functionalized nanoparticles. In other embodiments, the syringe is pre-loaded with the functionalized nanoparticles. In some embodiments, the syringe comprises a filter for removing the functionalized nanoparticles from a solution placed in the syringe prior to or during injection.

In some embodiments, the kits described herein comprise instructions for use.

Exemplary embodiments of the disclosure will be described in more detail by the following examples. These embodiments are exemplary of the disclosure, which one skilled in art will recognize is not limited to the exemplary embodiments.

EXAMPLES

Example 1: Crystallization of a Chemical or Pharmaceutical Compound

Generally, the disclosure presents a process for crystallizing organic or inorganic compounds using nanoparticles surface coated with functional groups, comprising the following steps:

i. A saturated solution of compound is prepared by making a suspension of compound in corresponding solvent at room temperature. The suspension is stirred for 24 hours and then filtered with a 0.25-micron filter and a clear saturated solution as a filtrate is used;

ii. 1 ml of clear saturated solution is diluted with 50 μl of solvent in order to create an undersaturated solution;

iii. Amount of self-assembled gold or magnetic nanoparticles are calculated corresponding to 1 ml of antisolvent;

iv. The clear undersaturated solution is mixed with the calculated amount of self-assembled gold or magnetic nanoparticles to increase the supersaturation;

v. The system is mixed to produce a slurry of crystals of the organic and inorganic compounds;

vi. crystals of the organic or inorganic compounds are recovered from the slurry by filtration or centrifugation. In a case of magnetic nanoparticles a strong magnet separates the magnetic nanocrystals and the slurry is filtered to separate organic or inorganic compound crystals from solution.

TABLE 1

Examples of compounds of interest (solutes) and their solvents.

| Solute/Compound of Interest | Solvent |
|---|---|
| D-mannitol | Water |
| D-mannitol | Water:ethanol mixture (e.g., 85:15, 75:25, or 50:50% water:ethanol) |
| Fenofibrate | Ethyl acetate |
| Fenofibrate | Acetate-decane |
| Sodium chloride (NaCl) | Water |
| 4-Nitrophenol | Water |
| Benzoic acid | Water |

Example 2: Method to Purify Water

Nanoparticle crystallization can be used to purify water by reducing the concentration of dissolved solids, organic chemicals, and particulates present in water. Innovative process simplification and thermal optimization would minimize energy consumption. The new method may remove a broad spectrum of contaminants, without the need for expendable filters or membranes. FIG. 1 shows a schematic of a purification process. Water to be treated would pass through a column comprising an effective amount functionalized nanoparticles. In those and other embodiments, an effective amount refers to an amount of functionalized nanoparticles that can induce crystallization of impurities including unwanted solids, organic chemicals, and particulates comprised in the solution, e.g., water. Crystals of unwanted solids, organic chemicals, and particulates present would form inside the column and the purified water will pass through the column.

Figure 2:
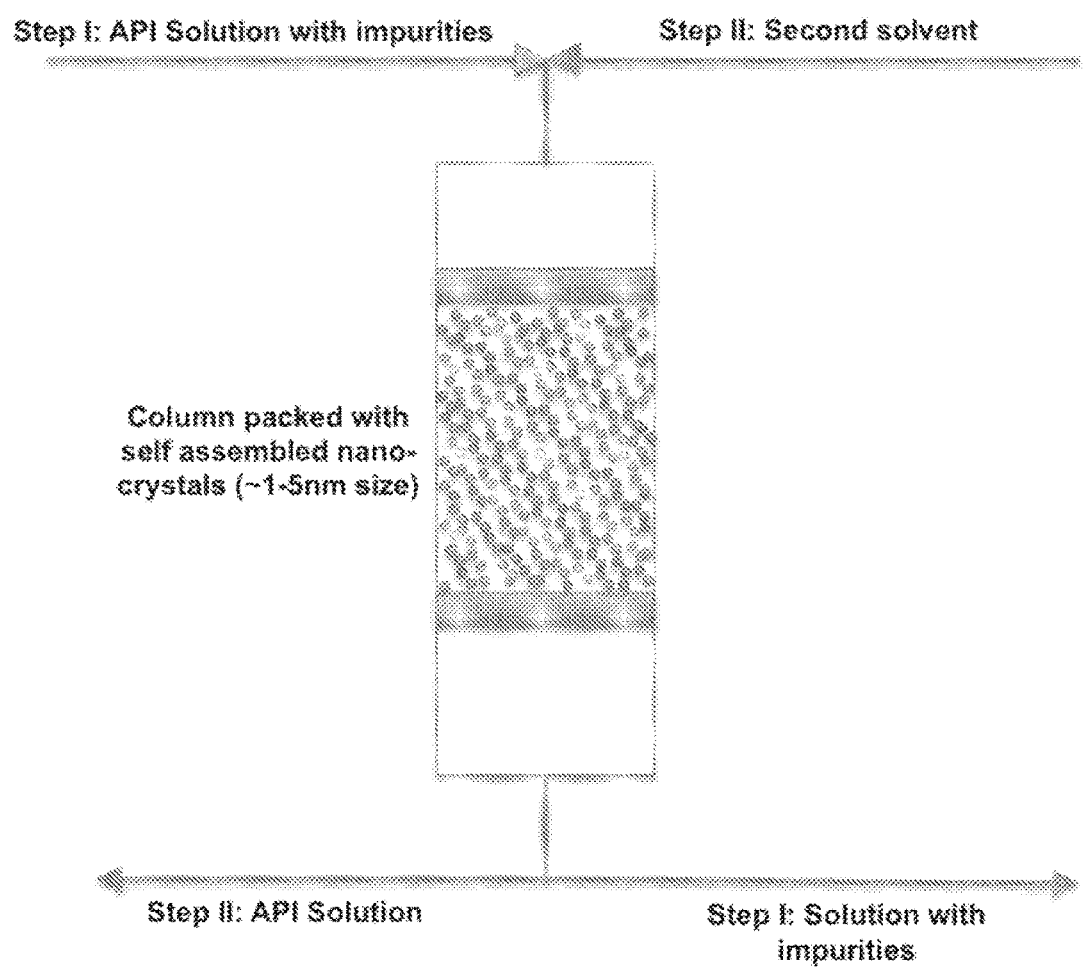
FIG. 2 is a schematic diagram of an API purification process using functionalized nanoparticles.

Example 3: Method to Purify Active Pharmaceutical Ingredients (API's) from its Impurities Nanoparticle crystallization may also be used to purify active pharmaceutical ingredients (API's) from its impurities. FIG. 2 shows a schematic of a purification process. API solution with its impurities to be treated would pass through a column comprising an effective amount of functionalized nanoparticles. In the first step, the API would crystallize inside the column and the solution of unwanted solids and impurities present would pass through the column. In the second step, the API crystals can be dissolved in another solvent, pass through the column, and can be crystallized outside of the column.

Example 4: Crystallization of Proteins and Biological Macromolecules

The lack of generalized methods for high quality crystal production for proteins and biological macromolecules is still a major bottleneck in the process of macro and large molecule crystallization. The new technology using functionalized nanoparticles could provide several macro and large molecule crystallization strategies, with an emphasis on advances and challenges facing researchers in the field today. Proteins have proven to be difficult to study owing to their partially hydrophobic surfaces, flexibility, and lack of stability. The new technical advances will lead to a rapid increase in the rate at which protein structures are solved in the near future.

Example 5: Preparations of Self-Assembled Monolayers (SAMs) of Functionalized Gold Nanoparticles Gold nanoparticles (GNPs) functionalized with thiol containing molecules forming self-assembling monolayers are often used as a heterogeneous surface to crystallize chemical and pharmaceutical compounds. In the present disclosure, functionalized nanoparticles were used to crystallize organic and inorganic compounds from undersaturated samples similarly as antisolvent crystallization. The knowledge of the surface coverage of functionalized nanoparticles is important to accurately determine the amount of nanoparticles required to replace the volume of antisolvent.

Figure 3A:
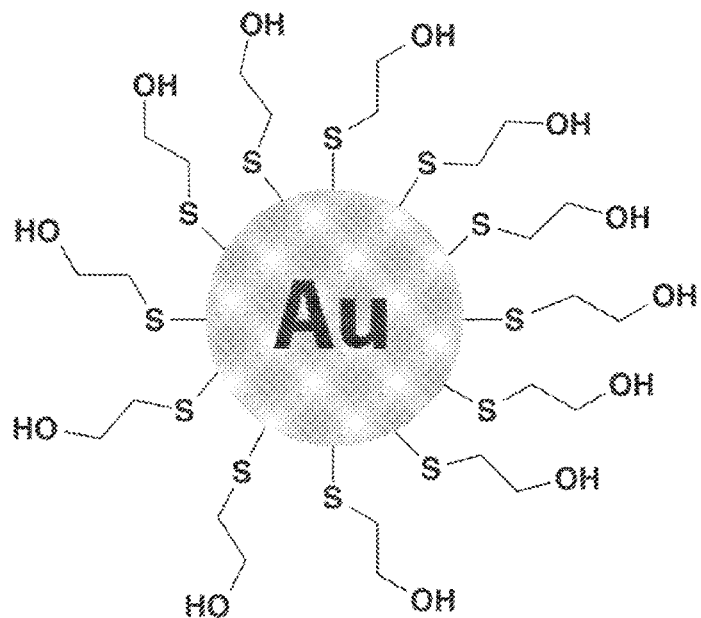
FIGS. 3A to 3B are schematics of bonding motifs between thiolates and gold (FIG. 3A) and carboxylates and iron oxide nanoparticles (IONPs) (FIG. 3B).
Figure 3B:
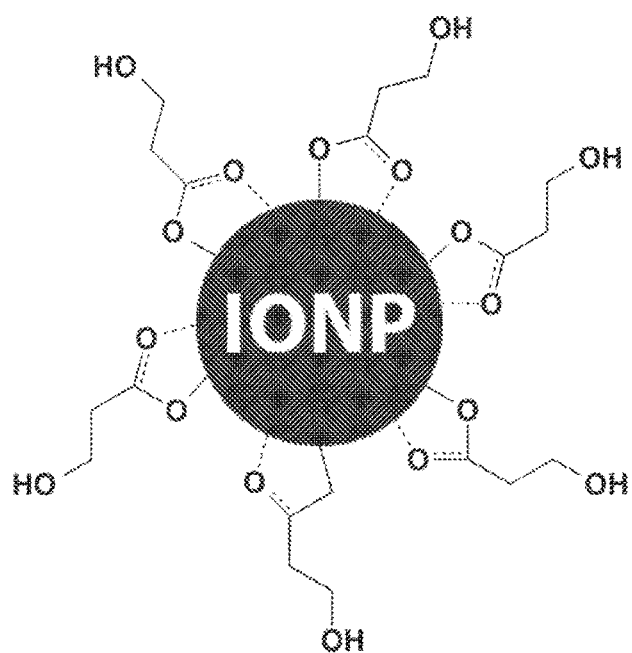

Self-assembled gold nanoparticles coated with 2-mercaptoethanol (1.8 and 5.0 nm size) were purchased from Nanopartz Inc. Loveland, Colo. (FIG. 3A). Iron Oxide Nanoparticles (IONPs) were synthesized by a chemical co-precipitation method under alkaline conditions and the molar ratio between $Fe^{2+}$ salt and $Fe^{3+}$ salt was maintained at 1:2. In order to synthesize 1 g of $Fe_3O_4$ particle, 0.86 g of $FeCl_2\_4H_2O$ and 2.35 g of $FeCl_3\_6H_2O$ were dissolved in 40 mL ultrapure water under $N_2$ atmosphere with vigorous stirring at a speed of 1000 rpm. As the solution was heated to 80° C., 5 mL of $NH_4OH$ solution was added, and the reaction was continued for another 30 min. The resulting suspension was cooled down to room temperature and washed with ultrapure water. The product of bare magnetic nanoparticles (IONP) was isolated from the solvent by magnetic decantation. The IONPs were further washed with water 5 times and separated by magnetic decantation. The IONPs were further coated by glycolic acid by mixing the IONPs with 10M solution of glycolic acid. The mixture was stirred for 24 hours at room temperature and the IONPs were separated by magnetic decantation (FIG. 3B).

Example 6: Crystallization of D-Mannitol in Water Using Gold Nanoparticles

A saturated solution of D-mannitol was prepared by making a suspension in water at room temperature. The suspension was stirred for 24 hours and then filtered with a 0.25-micron filter and a clear saturated solution as a filtrate was used. 1 ml of clear saturated solution was diluted with 50 µl of solvent in order to create an undersaturated solution. The clear undersaturated solution was mixed with 2.5 mg of 5 nm or 1.8 nm of functionalized gold or magnetic nanoparticles to increase the supersaturation. The solution with 5 nm functionalized gold nanoparticles was seeded with D-mannitol crystals to produce a slurry of crystals. In the case of a D-mannitol solution mixed with 1.8 nm functionalized gold nanoparticles, spontaneous crystallization was observed right after the addition of the nanocrystals. The crystals were centrifuged or filtered in order to separate the crystals from the nano-suspension.

Example 7: Quantification of Self-Assembled Monolayers by the Measurements of the Gold-to-Sulfur (Au/S) Ratio The determination of the functional group coverage via the gold-to-sulfur ratio is based on the fact that each functional group on the nanoparticle surface carries a single sulfur atom only while gold atoms constitute the voluminous particle core. Thus, gold increases with the cube, and sulfur with square, of the particle diameter D, providing a simple linear relationship between the Au/S ratio and D. The maximum ligand density versus nanoparticle diameter was theoretically calculated. If the surface coverage of a given functionalized group is known, then the amount of bound functional group can be calculated. Finally, the weight of ligand-covered 5 nm gold nanoparticles equivalent to 1 ml of ethanol was calculated. Table 2 shows the theoretical calculations.

TABLE 2

Calculation of Ligand Coverage vs GNP Size. The quantification was done in equivalence to 1 ml of ethanol.

| | | |
|---|---|---|
| Diameter of gold nanoparticle | | 5 nm |
| Volume per nano particles (Vnp) | 4/3 π r3 | 6.54E−20 cm3 |
| Surface area per nanoparticle (SAnp) | 4 π r2 | 7.85E−13 cm2 |
| Density (True Density) (Dnp) | | 19.32 g/cm3 |
| Mass per particle (Mnp) | Vnp * Dnp | 1.26E−18 g |
| Atomic weight of gold (Mau) | | 1.96E+02 g/mol |
| Average number of gold atoms per GNP (N(Au/GNP)) | (π/6) * (Dnp * (2r^3)/Mau) | 6.44263E−21 |
| Mass of gold particle per g | | 1.26E−18 g |
| Area covered by each ligand (AL) | | 2.14E−15 cm2 |
| Number of ligand on each particles | | 3.67E+02 |
| Number of ligand per g of gold nanoparticles | | 2.91E+20 |
| g weight of ligand covered gold particles equivalent to 1 ml of ethanol | | 3.54E+01 g |

TABLE 2-continued

Calculation of Ligand Coverage vs GNP Size. The quantification was done in equivalence to 1 ml of ethanol.

| | | |
|---|---|---|
| Density of ethanol (DEtOH) | | 7.89E−01 g/cm3 |
| | Density/mol wt | 1.71E−02 |
| OH group in 1 ml of Ethanol | | 1.03E+22 |

Figure 4A:
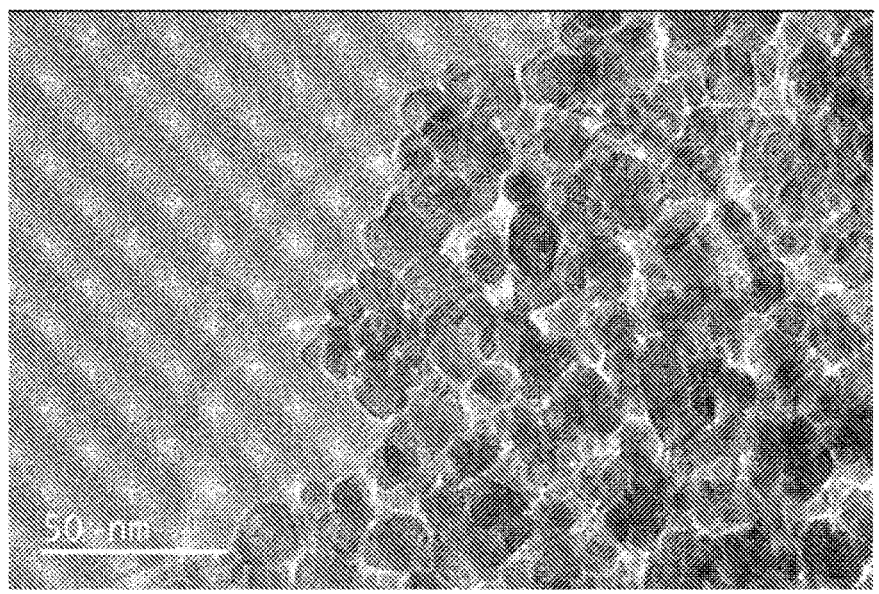
FIGS. 4A to 4B are TEM images of IONPs coated with glycolic acid. The scale bar of FIG. 4A is 50 nm and the scale bar of FIG. 4B is 20 nm. The IONPs are in the range of 5-15 nm in size.
Figure 4B:
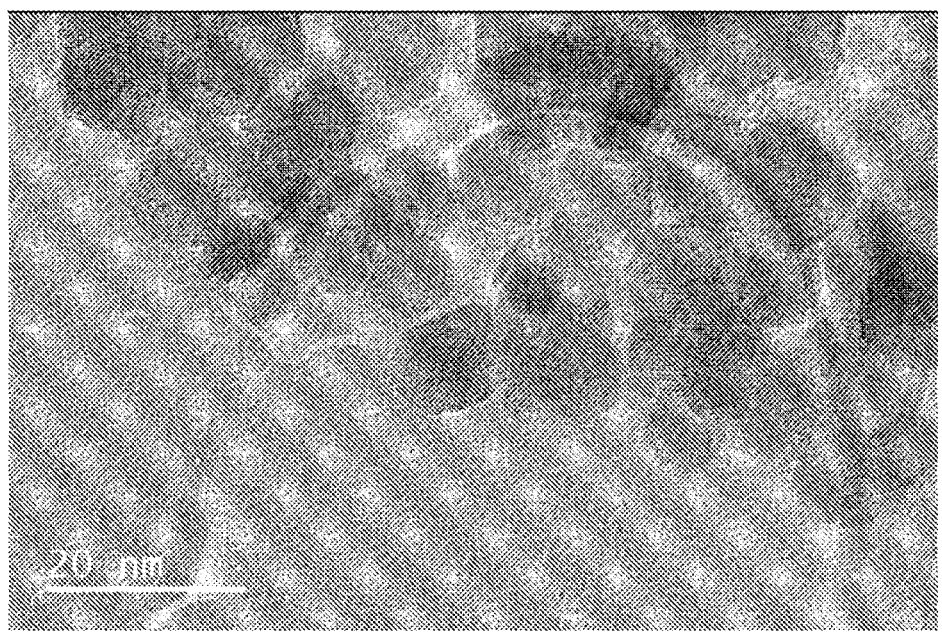

Example 8: Characterization of Self-Assembled Monolayers of Iron Oxide Nanoparticles The size and morphology of the IONPs were observed by transmission electron microscopy (TEM). A JEOL JEM 2010 transmission electron microscope operating at 200 kV was used. To prepare the nanoparticle samples, diluted drops of suspension were allowed to dry slowly on carbon-coated copper grids. FIGS. 4A to 4B show the glycolic acid coated IONPs, which are in the size range of 5-15 nm.

Figure 5:
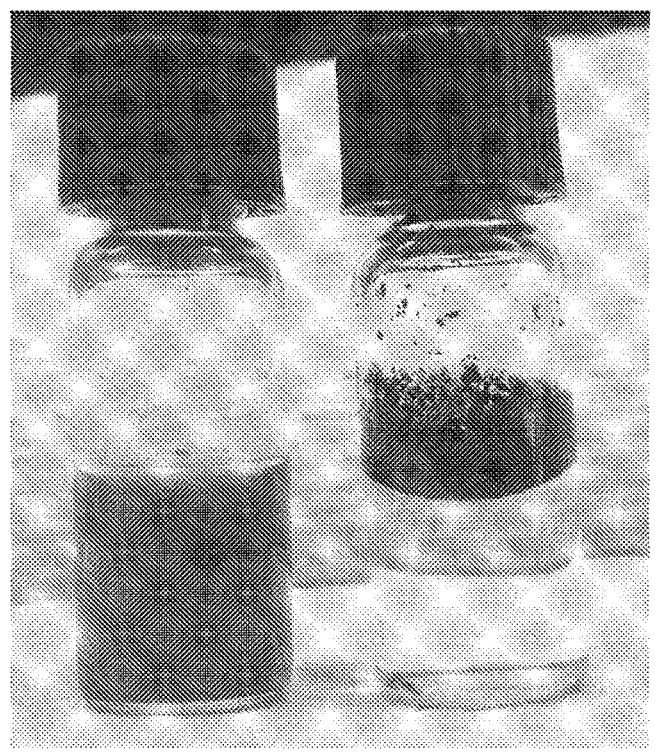
FIG. 5 is a picture showing the hydrophilic nature of IONPs coated with glycolic acid (left vial) and the hydrophobic nature of IONPs coated with decanoic acid in water solutions (right vial).

The hydrophilic and hydrophobic nature of IONPs coated with glycolic acid and decanoic acid is shown in FIG. 5 (left vial and right vial) where the hydrophilic glycolic acid self-assembled IONPs exist well suspended in water (left vial), while the hydrophobic decanoic acid self-assembled IONPs flocculated in the suspension in water (right vial).

Figure 6:
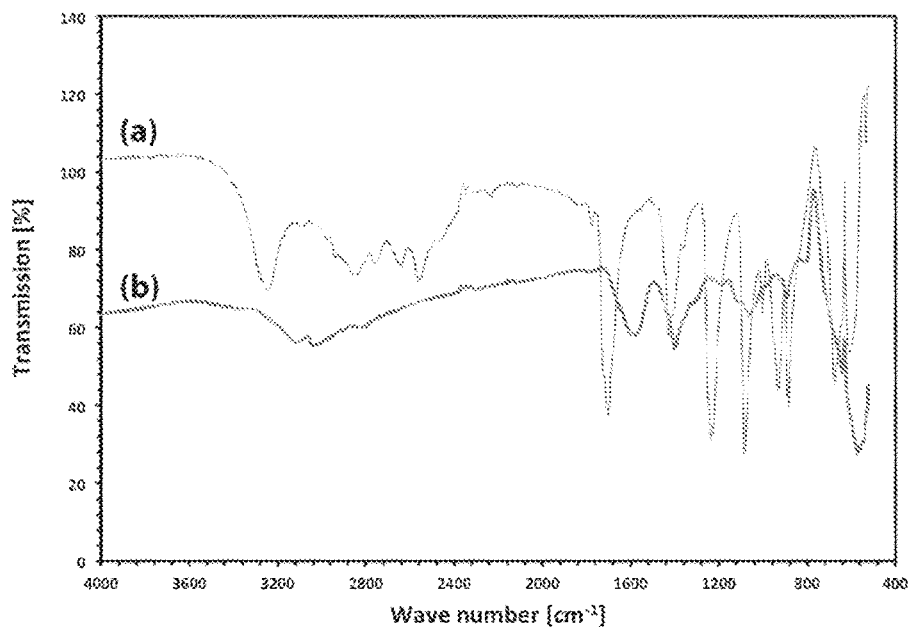
FIG. 6 is a FT-IR spectra of pure glycolic acid (line a) and iron oxide (line b) nanoparticles with self-assembled monolayers of glycolic acid.

The surface functionalization of the IONPs was analyzed by FT-IR. FIG. 6 shows the FT-IR spectrum of the IONP samples. The peaks at around 570 cm indicate the presence of iron oxide. The peaks at 1700 cm-1, representing the carbonyl stretching vibrations, were found to be shifted in the IONPs at lower wave numbers (1600 cm-1) due to the interaction of the IONP surface and the carboxylic group of glycolic acid.

Figure 7:
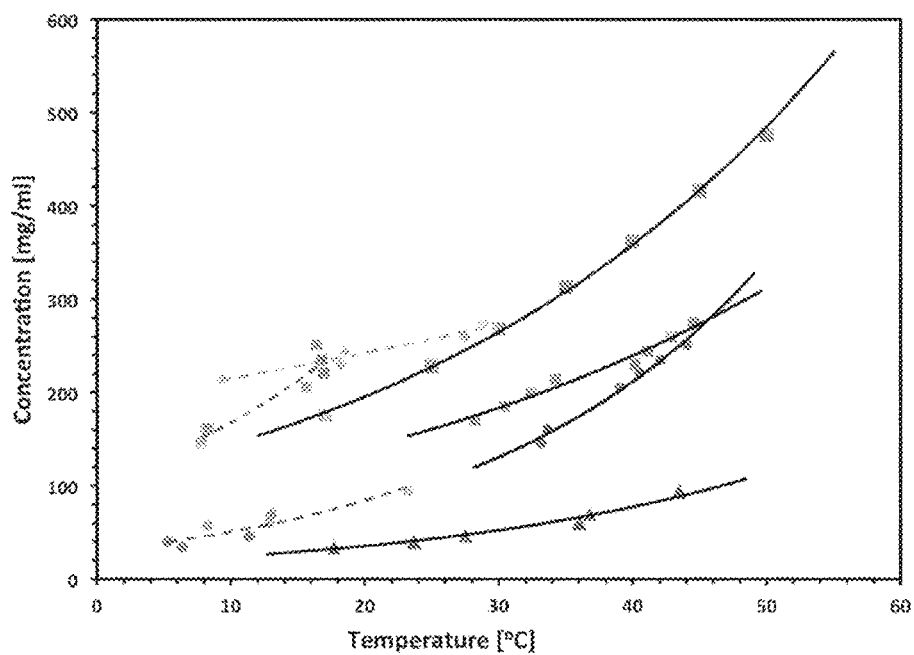
FIG. 7 is a graph showing the solubility of D-mannitol in water and water-ethanol mixtures. The line represents the guide to the eye through the saturation temperatures. The cross and circles are the average cloud points where the crystals were detected.
Figure 8A:
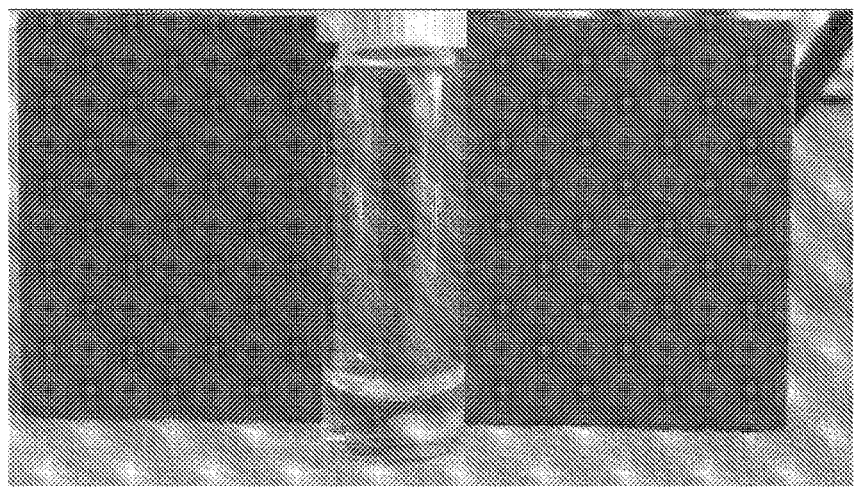
FIGS. 8A to 8C are images showing (FIG. 8A) a clear solution of D-Mannitol-water, (FIG. 8B) a solution after addition of 1.8 nm of functionalized gold nanoparticles in D-Mannitol-water, and (FIG. 8C) a crystallized sample of D-Mannitol-water after 15 minutes.
Figure 8B:
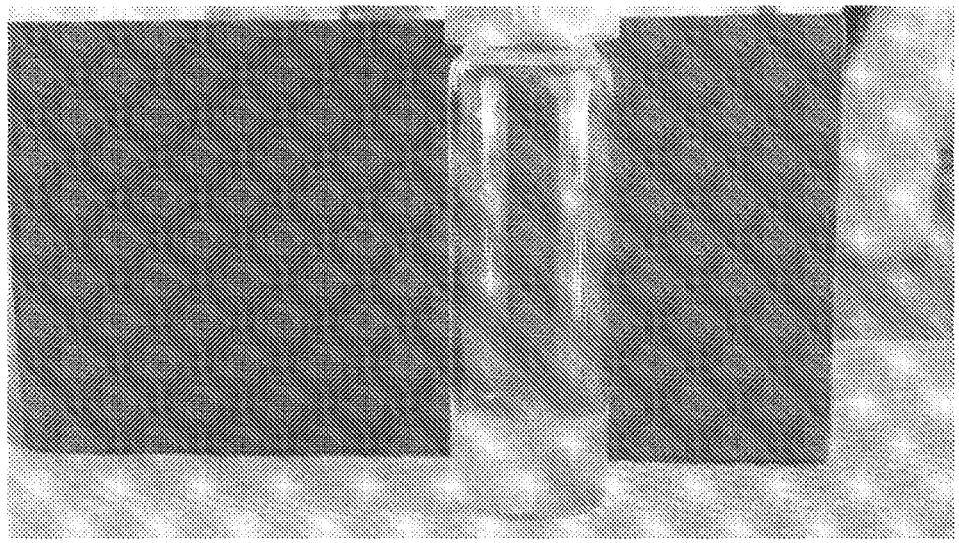
Figure 8C:
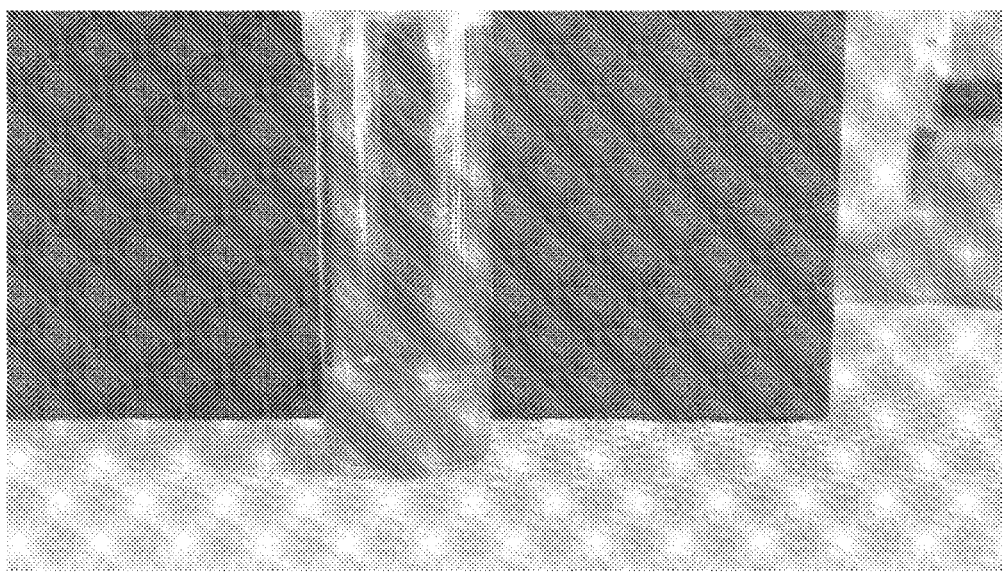
Figure 9:
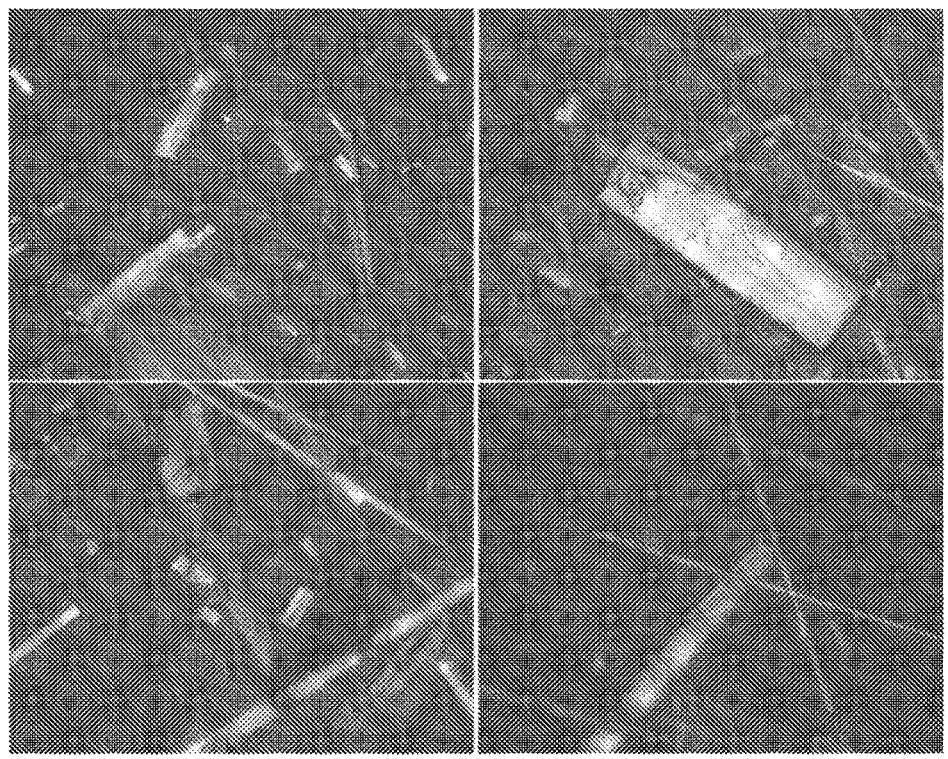
FIG. 9 shows microscope images of D-mannitol crystals in functionalized gold nanoparticles solution.

Example 9: Crystallization of D-Mannitol in Water Using Functionalized Nanoparticles The experimentally determined solubility and the metastable zone width (MSZW) of D-mannitol in water and water-ethanol mixtures (85-15, 75-25, and 50-50% wt/wt of water-ethanol mixtures) are shown in FIG. 7. According to the results of D-mannitol in water and water-ethanol mixtures, the solubility decreases with an increase in the amount of ethanol in water-ethanol mixtures. In order to know the required amount of functionalized nanoparticles and the operating region for crystallization, the MSZW of D-mannitol is important. For the samples of D-mannitol in the mixtures of 85-15 and 75-25% wt/wt of water-ethanol, the cloud point lies above the saturation temperature of D-mannitol in pure water. This means that, for the mixtures of 85-15 and 75-25% water-ethanol, and the solutes with a concentration of 193 mg/ml at 20° C., spontaneous nucleation will not occur because they will remain in solution. However, these experiments helped to determine the optimum operating supersaturation levels as well as the amount of antisolvent required to crystallize compounds at a given concentration. It also helped to determine if the samples need to be seeded or not. For the solutions of D-mannitol in 50-50% wt/wt water-ethanol mixtures, the cloud point lies well below the saturation temperature of D-mannitol in pure water. The cloud point refers to the temperature where the mixture starts to phase separate and two phases appear, thus becoming cloudy.

D-mannitol was crystallized in water using 5 nm and 1.8 nm functionalized nanoparticles. In the crystallization process with 5 nm functionalized gold nanoparticles, particle formation was not observed to occur immediately after the addition of functionalized nanoparticles to the drug solution. These results were not surprising given the nature and amount of functionalized gold nanoparticles (2.5 mg) added to the undersaturated solution of D-mannitol in water. The crystallization was observed to occur only after seeding the solution with D-mannitol seeds.

The solution after the addition of 5 nm size functionalized nanoparticles remains in the metastable zone width (MSZW) and crystallization without seeding only occurs after a long induction time. In the crystallization process with 1.8 nm functionalized gold nanoparticles, crystallization was observed to occur immediately after the addition of nanoparticles. As the size decreases, the surface area increases and the concentration of ligand increases with the square of particle diameter. The solution was in the supersaturated region after the addition of 1.8 nm gold nanoparticles, and spontaneous nucleation and crystallization occurred after 15 minutes as shown in FIGS. 8A to 8C and FIG. 9.

Figure 10:
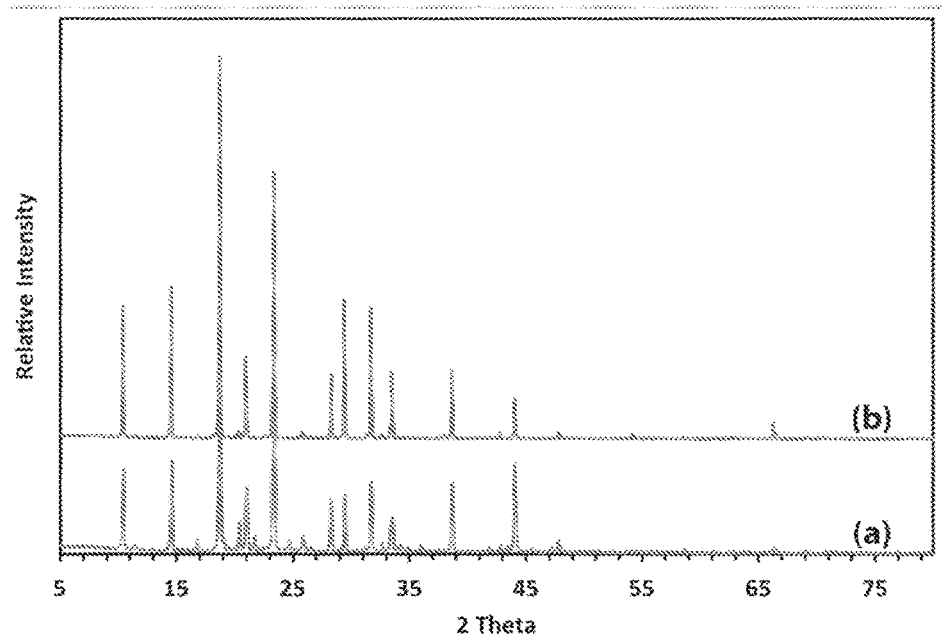
FIG. 10 shows powder x-ray diffraction (PXRD) of solids samples of D-Mannitol, (line a) in the starting material purchased from Sigma-Aldrich and (line b) in D-Mannitol crystallized from a water solution using functionalized gold nanoparticles.

A mixture of the β-form of D-mannitol and small traces of gold nanoparticles was the outcome from a PXRD analysis of the powder obtained after filtration (FIG. 10). The diffractograms (FIG. 10) recorded from the powder XRD of the sample show extra peaks at the 2θ position 38.13 (Bragg's plane 111), 44.35 (Bragg's plane 200), 64.73 (Bragg's plane 220), and 77.75 (Bragg's plane 311), indicating a structure of the GNPs. Tables 3 and 4 show the maximum ligand density versus nanoparticle diameter as theoretically calculated.

TABLE 3

Calculation of Ligand Coverage vs GNP Size.

Ethanol

| | | | |
|---|---|---|---|
| Diameter of particle | d | 5.00E−09 | m |
| Density of gold particles | ρ | 19320 | kg/m^3 |
| Decane Density | ρ$_{decane}$ | 789 | kg/m3 |
| Decane Mol wt | | 46.07 | kg/kmol |
| Area of each MercaptoEtOH | A (from literature) | 1.14E−19 | m^2 |
| MW of gold | | 196.9666 | kg/kmol |
| Area of each particle | 4 π r2 | 7.86E−17 | m^2 |
| Mass of each particle | 4/3 π r3 * ρ | 1.27E−21 | kg |
| No of ligands on each particle | 4 π r2/A | 6.89E+02 | |
| No of particles equivalent to 1 mL | | 1.50E+19 | |
| Mass of particles eq to 1 mL | | 1.89E−02 | kg |
| | | 1.89E+01 | g |
| 1 mL of dodecane | | 0.789 | g |
| | | 0.017126 | g mol |
| | | 1.03E+22 | molecules |

TABLE 4

Calculation of Ligand Coverage vs GNP Size.

Ethanol

| | | | |
|---|---|---|---|
| Diameter of particle | d | 1.80E−09 | m |
| Density of gold particles | ρ | 19320 | kg/m^3 |
| Decane Density | ρ$_{decane}$ | 789 | kg/m3 |
| Decane Mol wt | | 46.07 | kg/kmol |
| Area of each MercaptoEtOH | A (from literature) | 1.14E−19 | m^2 |
| MW of gold | | 196.9666 | kg/kmol |
| Area of each particle | 4 π r2 | 1.02E−17 | m^2 |
| Mass of each particle | 4/3 π r3 * ρ | 5.90E−23 | kg |

TABLE 4-continued

Calculation of Ligand Coverage vs GNP Size.

Ethanol

| | | | |
|---|---|---|---|
| No of ligands on each particle | 4 π r2/A | 8.93E+01 | |
| No of particles equivalent to 1 mL | | 1.15E+20 | |
| Mass of particles eq to 1 mL | | 6.82E-03 | kg |
| | | 6.82E+00 | g |
| 1 mL of dodecane | | 0.789 | g |
| | | 0.017126 | g mol |
| | | 1.03E+22 | molecules |

Example 10: Fenofibrate Crystallization

Figure 11:
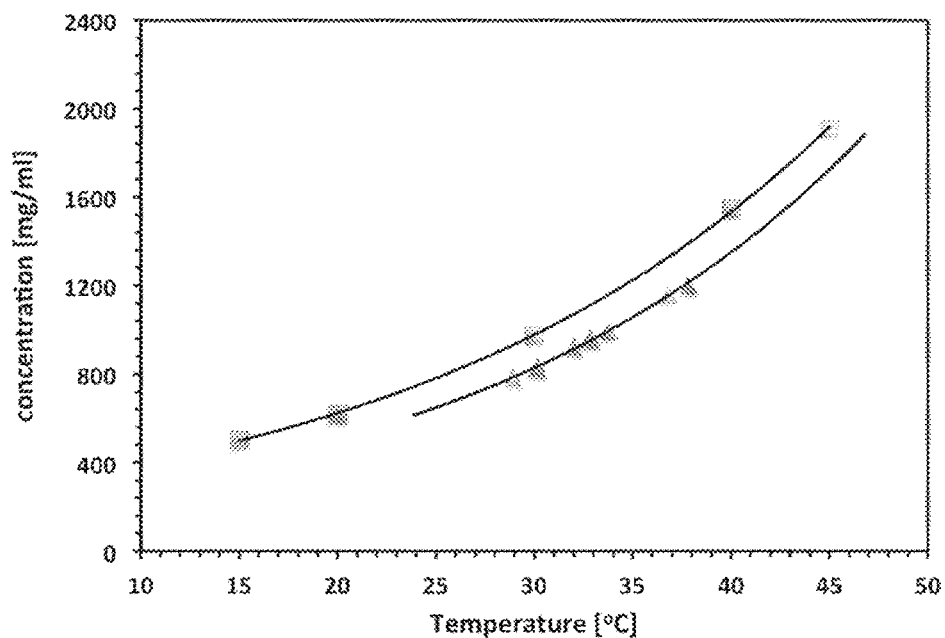
FIG. 11 is a graph showing the solubility of fenofibrate in ethyl acetate (boxes) and ethyl acetate-decane (triangles) (95-5% vol/vol) mixtures. The line represents the guide to the eye through the saturation temperatures.

The experimentally determined solubility of fenofibrate in ethyl acetate and ethyl acetate-decane mixtures (95-5% vol/vol) are shown in FIG. 11. The solubility of fenofibrate is lower in ethyl acetate-decane mixture (95-5% vol/vol) as compared to the solubility of fenofibrate in pure ethyl acetate.

Figure 12:
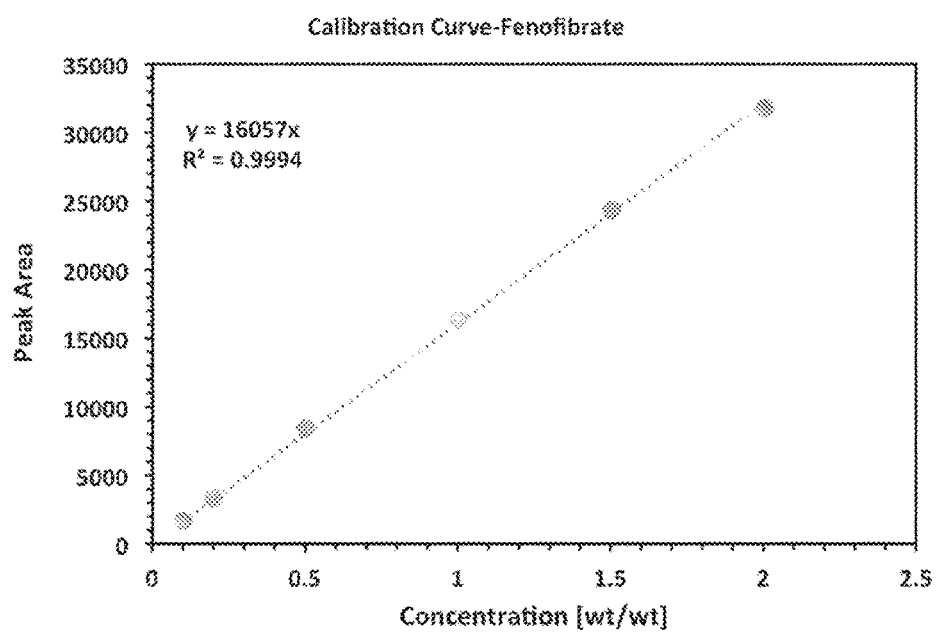
FIG. 12 is a graph showing the calibration curve for fenofibrate as generated by measuring the peak area and absorbance at 284 nm.

Example 11: Crystallization of Fenofibrate in Ethyl Acetate Using Functionalized Gold Nanoparticles Fenofibrate is highly soluble in ethyl acetate and slightly soluble in decane. In case of fenofibrate crystallization, ethyl acetate was used as a solvent and decane was used as an antisolvent. Fenofibrate was crystallized in ethyl acetate using 1.8 nm functionalized nanoparticles using 1-Decanethiol. In the crystallization process with 1.8 nm functionalized gold nanoparticles, crystallization was not observed to occur immediately after addition of functionalized nanoparticles to the drug solution (FIG. 12). These results were not surprising given the nature and amount of functionalized gold nanoparticles (2.5 mg) added to the undersaturated solution of fenofibrate in ethyl acetate. Similar to D-mannitol, the crystallization was observed to occur only after seeding the solution with fenofibrate seeds.

The sample was filtered using a 0.2 µm filter and solids were analyzed using PXRD. The filtered solution was then centrifuged to separate the gold nanoparticles and the clear solution was analyzed using the HPLC to determine the change in concentration. At 20 OC, the saturation concentration of fenofibrate in ethyl acetate was 618.9 mg/ml and after crystallization the concentration was 614.37 mg/ml of ethyl acetate. Therefore, the change in concentration after crystallization was 4.56 mg/ml of ethyl acetate and as per the solubility curve in pure ethyl acetate and mixture of ethyl acetate-decane, approximately or less than 0.125% of 1-decane was required to obtain the concentration difference of 4.5 mg/ml of fenofibrate in ethyl acetate.

Based on the concentration difference obtained using HPLC, the amount of 1.8 functionalized nanoparticles was calculated based on 0.125% of 1-decane required in order to achieve a concentration difference of 4.5 mg/ml of fenofibrate in ethyl acetate.

Figure 13:
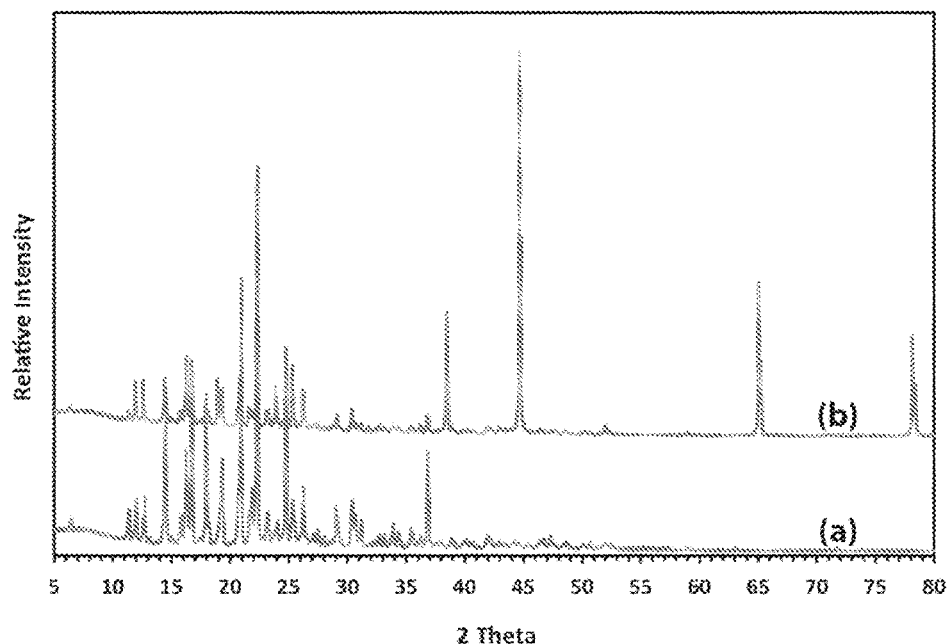
FIG. 13 shows PXRD of solids samples of fenofibrate, (line a) in the starting material purchased from Sigma-Aldrich and (line b) in fenofibrate crystallized from an ethyl acetate solution using functionalized gold nanoparticles.

As per the calculation, approximately 0.0048 g of 1.8 nm self-assembled gold nanoparticles are required to achieve a concentration difference of 4.56 mg/ml. Similar to D-mannitol, the diffractograms (FIG. 13) recorded from the powder XRD of sample show extra peaks at the 2θ position 38.13 (Bragg's plane 111), 44.35 (Bragg's plane 200), 64.73 (Bragg's plane 220), and 77.75 (Bragg's plane 311), indicating a structure of the GNPs. Tables 5, 6, and 7 show the maximum ligand density versus nanoparticle diameter as theoretically calculated.

TABLE 5

Calculation of Ligand Coverage vs GNP Size. The quantification was performed in equivalence to 1 ml of 1-decane.

Decane

| | | | |
|---|---|---|---|
| Diameter of particle | D | 1.80E-09 | m |
| Density of gold particles | P | 19320 | kg/m^3 |
| Decane Density | $\rho_{decane}$ | 730 | kg/m3 |
| Decane Mol wt | | 142.25 | kg/kmol |
| Area of each Mercaptodecane | A (from literature) | 2.14E-19 | m^2 |
| MW of gold | | 196.96657 | kg/kmol |
| Area of each particle | 4 π r2 | 1.02E-17 | m^2 |
| Mass of each particle | 4/3 π r3 * ρ | 5.90E-23 | kg |
| No of ligands on each particle | 4 π r2/A | 4.76E+01 | |
| No of particles equivalent to 1 mL | | 6.50E+19 | |
| Mass of particles eq to 1 mL | | 3.83E-03 | kg |
| Mass of particles eq to 1 mL | | 3.83E+00 | g |
| Mass of particles eq to 0.125% | | 0.0048 | g |
| 1 mL of decane | | 0.73 | g |
| | | 0.00513181 | g mol |
| | | 3.09089E+21 | molecules |

TABLE 6

Calculation of Ligand Coverage vs GNP Size.

Decane

| | | | |
|---|---|---|---|
| Diameter of particle | d | 5.00E-09 | m |
| Density of gold particles | ρ | 19320 | kg/m^3 |
| Decane Density | $\rho_{decane}$ | 730 | kg/m3 |
| Decane Mol wt | | 142.25 | kg/kmol |
| Area of each Mercaptodecane (A) | A (from literature) | 2.14E-19 | m^2 |
| MW of gold | | 196.96657 | kg/kmol |
| surface area per nanoparticle | 4 π r2 | 7.86E-17 | m^2 |
| Mass of each particle | 4/3 π r3 * ρ | 1.27E-21 | kg |
| No of ligands on each particle | 4 π r2/A | 3.67E+02 | |
| No of particles equivalent to 1 mL | | 8.42E+18 | |
| Mass of particles eq to 1 mL | | 1.06E-02 | kg |
| | | 1.06E+01 | g |
| 1 mL of dodecane | | 0.73 | g |
| | | 0.00513181 | g mol |
| | | 3.09089E+21 | molecules |

TABLE 7

Calculation of Ligand Coverage vs GNP Size.

Decane

| | | | |
|---|---|---|---|
| Diameter of particle | d | 1.80E-09 | m |
| Density of gold particles | ρ | 19320 | kg/m^3 |
| Decane Density | $\rho_{decane}$ | 730 | kg/m3 |
| Decane Mol wt | | 142.25 | kg/kmol |
| Area of each Mercaptodecane | A (from literature) | 2.14E-19 | m^2 |
| MW of gold | | 196.96657 | kg/kmol |
| Area of each particle | 4 π r2 | 1.02E-17 | m^2 |
| Mass of each particle | 4/3 π r3 * ρ | 5.90E-23 | kg |
| No of ligands on each particle | 4 π r2/A | 4.76E+01 | |
| No of particles equivalent to 1 mL | | 6.50E+19 | |

TABLE 7-continued

Calculation of Ligand Coverage vs GNP Size.

Decane

| Mass of particles eq to 1 mL | 3.83E−03 | kg |
| --- | --- | --- |
| | 3.83E+00 | g |
| 1 mL of dodecane | 0.73 | g |
| | 0.00513181 | g mol |
| | 3.09089E+21 | molecules |

Example 12: Sodium Chloride Crystallization

Figure 14:
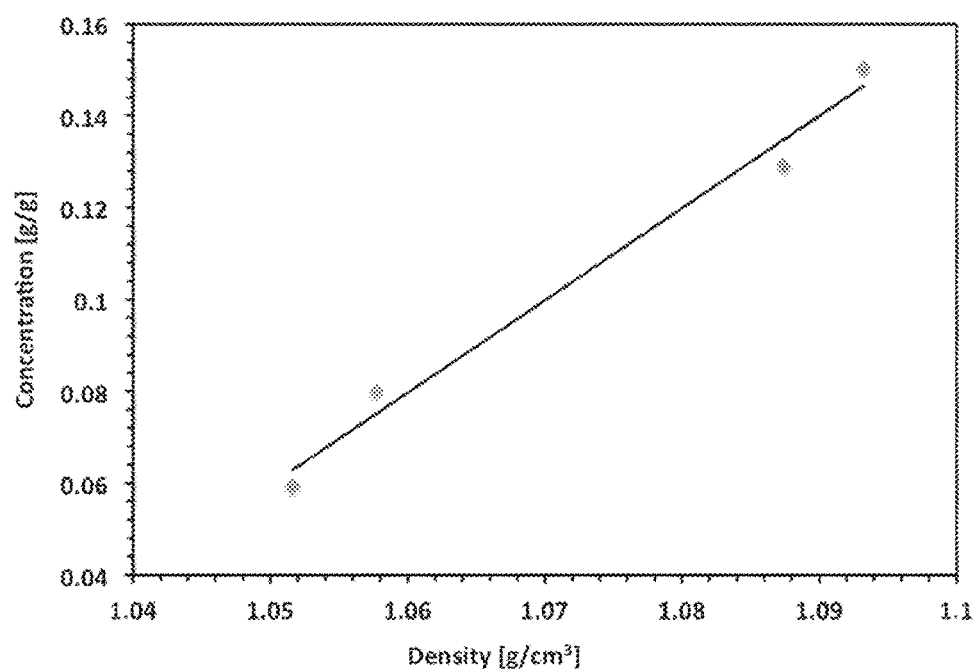
FIG. 14 is a graph showing the calibration curve for NaCl as generated by measuring the density by Digital Density Meter DMA4500 at different concentrations of NaCl water solutions.
Figure 15:
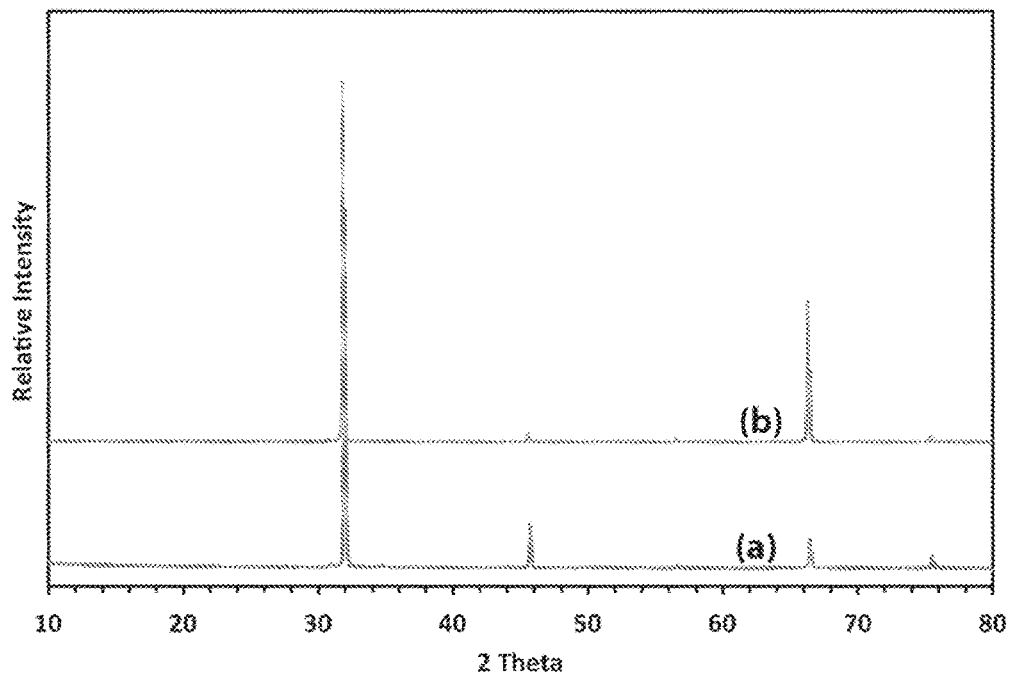
FIG. 15 shows PXRD of solid samples of NaCl, (line a) in the starting material purchased from Sigma-Aldrich and (line b) in the NaCl crystallized from a water solution using functionalized gold nanoparticles.

The antisolvent crystallization of NaCl is the best example of the influence of agglomeration on the final product purity. Though the crystals are crystallized from a mother liquor containing as much as 50% weight antisolvent (on a solvent basis), the uptake of the antisolvent is as low as 30 ppm. In the present study, functionalized nanoparticles were used to crystallize NaCl from a water solution. NaCl is highly soluble in water and slightly soluble in ethanol. In the case of NaCl crystallization, water was used as a solvent and ethanol was used as an antisolvent. NaCl was crystallized in water using 1.8 nm functionalized nanoparticles with an ethanol group at the open terminal. In the crystallization process with 1.8 nm functionalized gold nanoparticles, crystallization was not observed to occur immediately after addition of functionalized nanoparticles to the drug solution. After 4 hours the sample was seeded with NaCl crystals and the sample was crystallized only after 16 hour of stirring. The initial and final concentration of NaCl was measured using the Digital Density Meter DMA4500. This instrument is used for accurate measurements of solvent density necessary for the concentration measurements. FIG. 14 shows the calibration curve for NaCl as generated by measuring the density by Digital Density Meter DMA4500 at different concentrations of NaCl water solutions. The change in concentration after crystallization measured using the digital density meter was 27 mg. FIG. 15 shows the PXRD of solid samples of NaCl starting material purchased from Sigma-Aldrich and NaCl solids crystallized from a water solution using functionalized gold nanoparticles.

Figure 16:
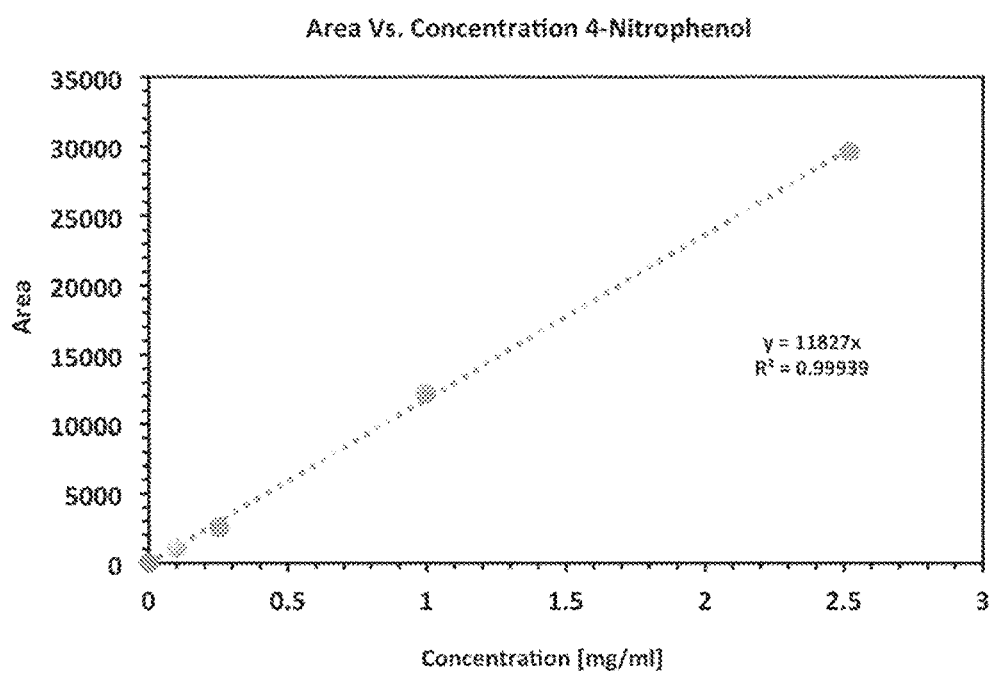
FIG. 16 is a graph showing the calibration curve for 4-nitrophenol as generated by measuring the peak area and absorbance at 230 nm.

Example 13: Improved Solubility of 4-Nitrophenol Using Functionalized Iron Oxide Nanoparticles The solubility of any molecule is a function of the free energy of the solid and of the molecule in the solution state. Whereas the free energy of the solid is an intrinsic property of that material, the free energy of the solution state is dependent on the solvent and the concentration of the solute in the solvent. At the equilibrium solubility, the free energy of the solid equals that of the solution. Therefore, the solubility of the drug substance can be increased by modifying its free energy by chemical (salt, co-crystal, polymorph or co-solvent) or physical (amorphous, size reduction) means. A controlled approach to enhancing solubility is to use co-solvent. Co-solvents are water miscible solvents that facilitate aqueous solubility. The most commonly used co-solvents are glycerin, propylene glycol, polyethylene glycol 400, and ethanol. Typically, solubility increases in a logarithmic fashion with the increasing fraction of the co-solvent. However, there may be physicochemical, regulatory, or safety considerations that constrain the absolute amount of the co-solvent used. The key is to use functionalized nanoparticles as a species to increase the equilibrium saturation by increasing the solubility. The main advantage of using functionalized iron oxide nanoparticles is the ease of separation before the final application. 4-nitrophenol was used as a model compound, which is modestly soluble in water (13 g/L at 25° C.). The suspension of 4-nitrophenol (4-NP) was prepared (2 ml suspensions with 20 g/L concentration of 4-NP in water) and 200 mg of IONPs functionalized with glycolic acid were added. The IONPs were separated using a strong magnet and the solution of 4-NP in water was clear. The clear solution was analyzed using HPLC in order to determine the final concentration. FIG. 16 shows the calibration curve for 4-NP as generated by measuring the peak area and absorbance at 230 nm.

Figure 17:
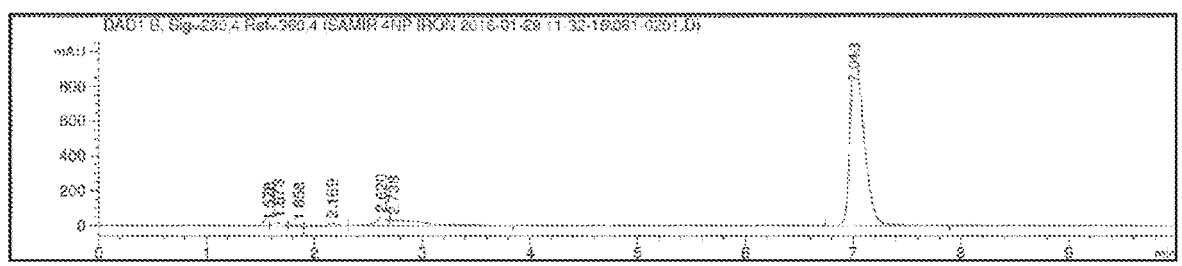
FIG. 17 is a high performance liquid chromatography (HPLC) chromatogram for the determination of 4-nitrophenol in water at a wavelength of 230 nm. The peak at 7.013 minutes corresponds to 4-nitrophenol.
Figure 18:
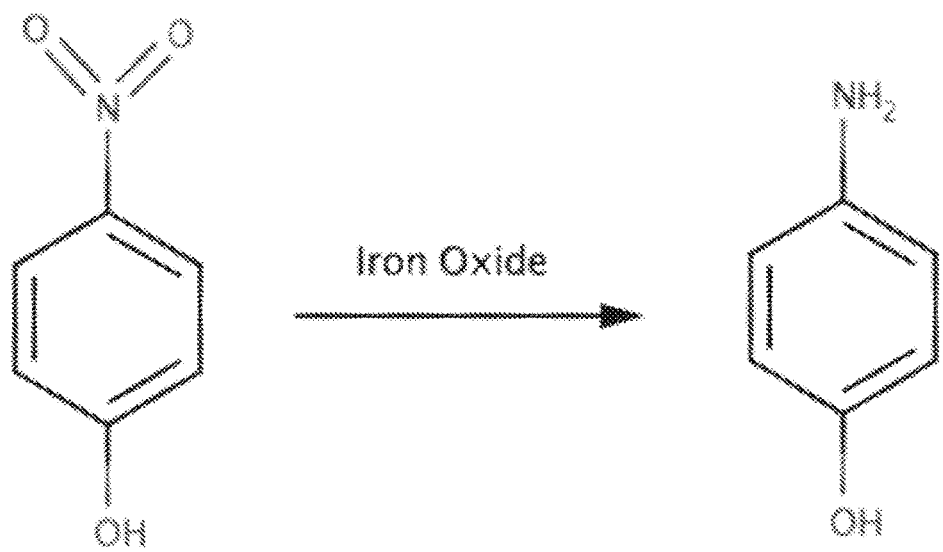
FIG. 18 is a schematic of the conversion of 4-nitrophenol to 4-aminophenol in the presence of iron oxide as a catalyst.

The sample measured by HPLC shows the concentration of 16.5 g/L, which was less than the initial concentration (20 g/L). The part of 4-nitrophenol was catalyzed to 4-Aminophenol by iron oxide as a catalyst. FIG. 18 shows a schematic of the conversion of 4-nitrophenol to 4-aminophenol in the presence of iron oxide as a catalyst. The HPLC results show additional retention peaks at 2.6 and 2.7 minutes, which correspond to 4-aminophenol (FIG. 17).

Figure 19:
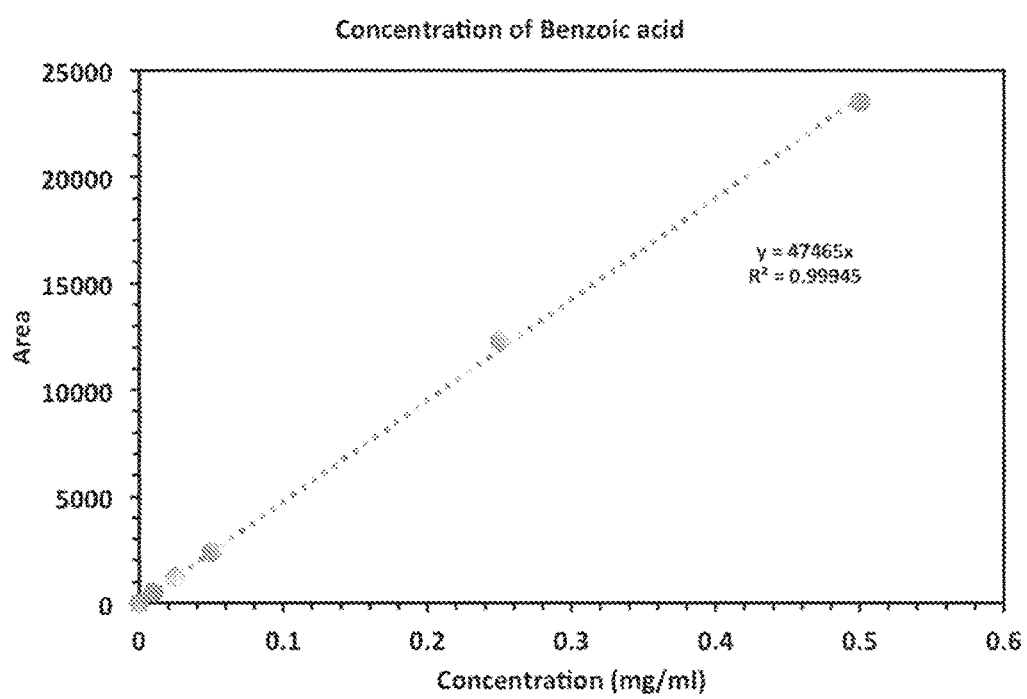
FIG. 19 is a graph showing the calibration curve for benzoic acid as generated by measuring the peak area and absorbance at 230 nm.

Benzoic acid was used as another model compound, which is modestly soluble in water (3.5 g/L at 25° C.). The suspension of benzoic acid was prepared (2 ml suspensions with 20 g/L concentration of benzoic acid in water) and 500 mg of IONPs functionalized with glycolic acid were added. The IONPs were separated using a strong magnet and the solution of benzoic acid in water was clear. The clear solution was analyzed using HPLC in order to determine the final concentration. FIG. 19 shows the calibration curve for benzoic acid as generated by measuring the peak area and absorbance at 230 nm. The sample measured by HPLC shows a concentration of 20 g/L, which is more than 5 times higher than the equilibrium solubility of benzoic acid in water at 25° C.

Materials and Methods

D-mannitol, fenofibrate, and sodium chloride with purities of ≥99%, ≥99% and ≥99%, respectively, were obtained from Sigma Aldrich. DI-water, ethyl acetate, and decane were also obtained from Sigma Aldrich. Self-Assembled Gold nanoparticles coated with 2-mercaptoethanol (1.8 and 5.0 nm size) and 1-mercaptodecane (1.8 nm size) were purchased from Nanopartz Inc. Loveland, Colo.

HPLC Method for Fenofibrate

Fenofibrate raw materials were obtained directly from manufacturers in China. Acetonitrile and methanol were of HPLC grade, and trifluoroacetic acid was of spectrophotometric grade obtained from Sigma Aldrich. The water used was distilled then deionized in a Barnstead™ Nanopure™ II system (Sybron/Barnstead, Boston, Mass.).

The liquid chromatograph consisted of an HP 1090 M HPLC with a pump, an injector, an autosampler, a variable wavelength detector (HP 1050), and a diode array detector. The column was a Symmetry ODS 3.5 mm (100×4.6 mm) (Waters, Milford, Mass.).

Mobile Phase

The eluent consisted of acetonitrile-water-trifluoroacetic acid 700/300/1 (v/v/v) filtered through a 0.45 mm nylon filter. The flow rate was 1 ml min$^{-1}$.

Solutions

Fenofibrate reference standard and raw materials were dried under pumping vacuum at 60° C. for 2 h prior to use. The following solutions were prepared using acetonitrile and sonicated in an ultrasonic bath, when necessary, to dissolve the compounds: (1) a standard solution of 1 mg ml-1 (accurately known) fenofibrate reference standard, and (2) a test solution of 1 mg ml-1 (accurately known) fenofibrate raw material, and a UV detector set at 280 nm.

HPLC Method for 4-Nitrophenol and Benzoic Acid

An HPLC method for the determination 4-nitrophenol and benzoic acid has been developed and validated. The method development involved the study of methanol and acetonitrile as organic modifiers, pH and flow-rate using a Chromolith RP-18e (150 mm×4.6 mm I.D.) column. After comparing the performance the optimum analysis of these compounds was achieved using 50 mM acetate buffer (pH 5.0)-acetonitrile (80:20, v/v) as mobile phase, 1 mL min-1 flow-rate and UV detection at maximum absorbance wavelength of 250 nm.

Solubility Measurements

The solubility and metastable zone width (MSZW) of D-mannitol was measured in pure DI water and DI water-ethanol mixtures at different concentrations by adding a known amount of D-mannitol and 1 mL of solvent or solvent mixtures respectively to a 1.5 mL glass vial. The vials were then placed in the Crystal16 and the heating rate and cooling rate were set to 0.3° C./min. The samples were stirred with a controlled stirring speed of 700 rpm using magnetic stirring bars. The samples were heated with a heating rate of 0.3° C./min from 5° C. to 60° C. The temperature at which the suspension turned into a clear solution was recorded and assumed to be the saturation temperature. After a waiting time of 30 minutes at 60° C. the clear solution was cooled to 5° C. with a cooling rate of 0.3° C./min to recrystallize the mannitol. The temperatures at which the crystals are detected are assumed to be a cloud point. The same temperature profile was repeated three times for each sample. A fit of the Van't Hoff equation to the data facilitated the interpolation of the solubility as well as the determination of the prevailing supersaturation ratio $S=x/x^*$ in a certain solution composition.

Solubility Enhancement Technique Using Functionalized Nanoparticles

The solubility of a poorly water-soluble drug can be increased frequently by the addition of a water miscible solvent in which the drug has good solubility, known as co-solvents. Co-solvents are mixtures of water and one or more water-miscible solvents used to create a solution with enhanced solubility for poorly soluble compounds. Historically, this is one of the most widely used techniques because it is simple to produce and evaluate. Examples of solvents used in co-solvent mixtures are PEG 300, propylene glycol, or ethanol. Co-solvent formulations of poorly soluble drugs can be administered orally and parenterally. In the present study, functionalized nanoparticles can be used as replacement to co-solvents. The equilibrium solubility of 4-nitrophenol and benzoic acid was measured at room temperature using HPLC. A sample was prepared using a suspension stirred for 24 hours with excess of solid. The suspension was then filtered using 0.25-micron filter and the filtrate was used to determine the equilibrium solubility. The equilibrium solubility of 4-nitrophenol at 20° C. was 13 mg/ml and for benzoic acid was 3.5 mg/ml. A 20 mg sample of benzoic acid and 4-nitrophenol was weighed in a vial and 1 ml of water was added. The sample was stirred for 1 hour and 500 mg of functionalized IONPs (glycolic acid as a functional group) was added. The sample was then stirred for two hours and the magnetic particles were separated using a strong magnet and the clear sample was analyzed using HPLC to determine the final concentration dissolved.

Example 14: Functionalization of Silica Coated Iron Oxide Nanoparticles

Silica coated iron oxide nanoparticles were functionalized with silanes. The silanes (purchased from Gelest) are shown in Table 8. Silanes functionalized with alcohols (e.g. Si(OEt)3-CH2-CH2-OH) were not available for this investigation since these molecules are not stable due to self-condensation.

TABLE 8

Summary of the silanes under investigation.

| Name | Formula | Ref. number |
|---|---|---|
| ACETOXYETHYLTRIETHOXYSILANE | | SIA0025.0 |
| 2-CYANOETHYLTRIETHOXYSILANE | | SIC2445.0 |

TABLE 8-continued

Summary of the silanes under investigation.

| Name | Formula | Ref. number |
|---|---|---|
| HEXYLTRIETHOXYSILANE | 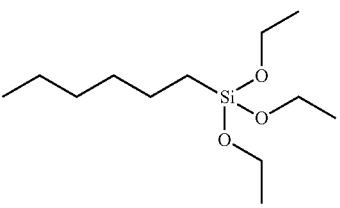 [SMILES: CCCCCC[Si](OCC)(OCC)OCC] | SIH6167.5 |
| N-DECYLTRIETHOXYSILANE | 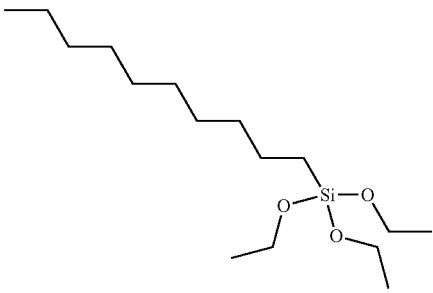 [SMILES: CCCCCCCCCC[Si](OCC)(OCC)OCC] | SID2665.0 |
| 2-[METHOXY(POLYETHYLENEOXY)6-9PROPYL]TRIMETHOXYSILANE | 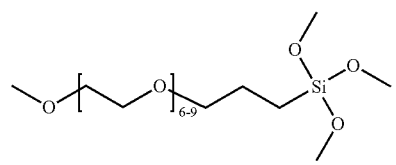 | SIM6492.7 |

Figure 20:
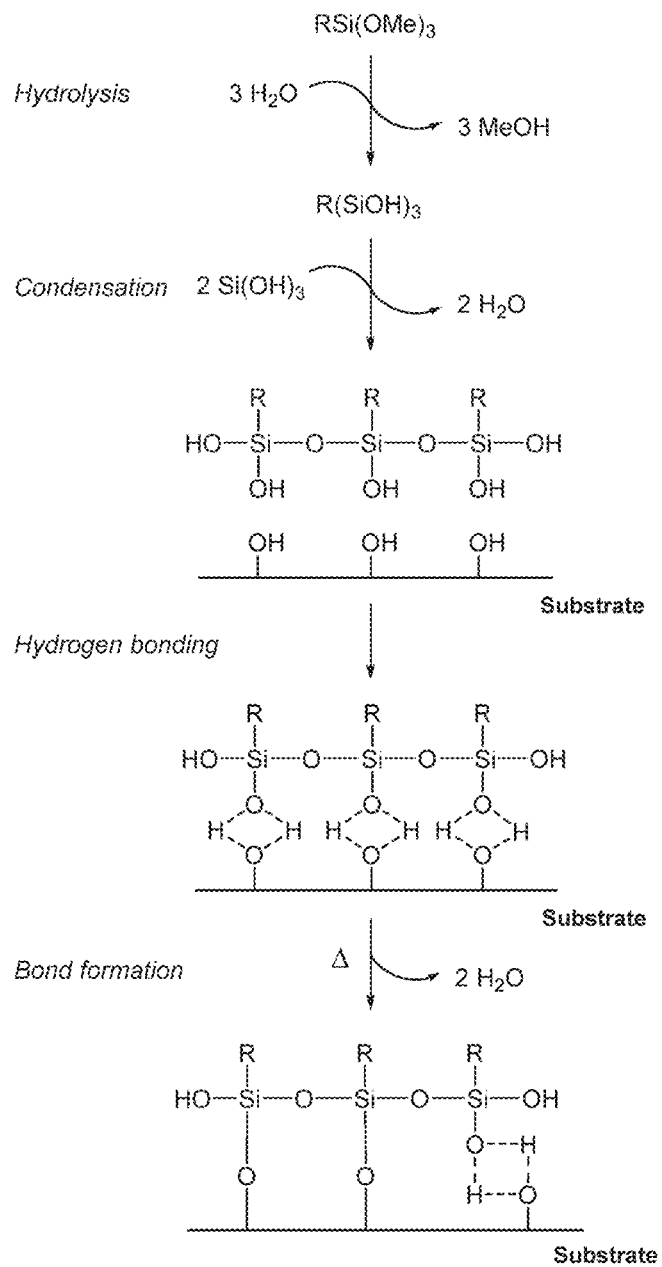
FIG. 20 is a schematic of a mechanism of silane deposition on the surface of a core-shell nanoparticle.

FIG. 20 shows the scheme of the mechanism of silane deposition on the silica surface.

200 nm silica coated iron oxide was functionalized with hexane (i.e. with silane SIH6167.5) as follows. (i) 5 mg of nanoparticles were washed with water and then with anhydrous ethanol. The solvent was then removed by magnetic separation. (ii) A solution of 95% w/w anhydrous ethanol+ 5% w/w water acidified at pH ~4 with acetic acid was prepared. Silane was added to reach a 2% w/w concentration. The solution was sonicated for 2 minutes in a bath sonicator. (iii) 1 mL of the reaction mixture was added to the washed nanoparticles and the mixture was vortexed. (iv) The reaction was performed at 25° C. under shaking at 500 rpm for 24 h. (v) The nanoparticles were dried for 2 h in an oven at 90° C. (vi) The nanoparticles were washed with ethanol by using the tip sonicator to properly redisperse and removing the solvent by magnetic separation.

Figure 21:
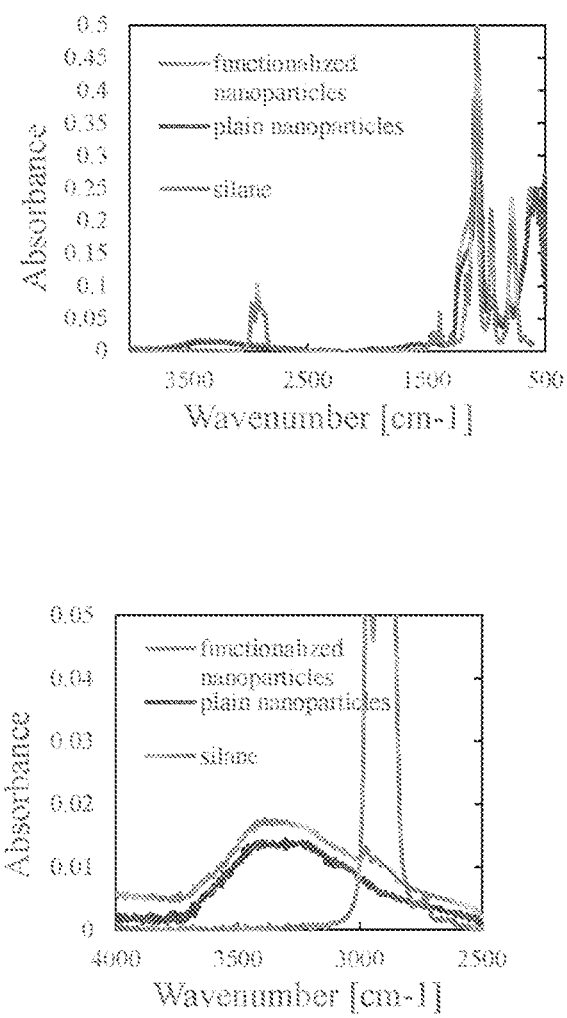
FIG. 21 is a series of graphs showing the FTIR spectrum of silica coated iron oxide nanoparticles functionalized with hexane. As a comparison, the FTIR spectra of the plain nanoparticles and of the silane are also shown. The spectra on the top of the figure are similar to those on the bottom but with a different scale.

The functionalized nanoparticles were analyzed by Fourier-transform infrared spectroscopy (FTIR) and the results are shown in FIG. 21. As comparison, the FTIR spectra of the non-functionalized nanoparticles and of the silane are also shown. The small peak at around 3000 cm$^{-1}$ corresponds to the stretching of the C—H bond, which suggests that the functionalization was successful.

Figure 22:
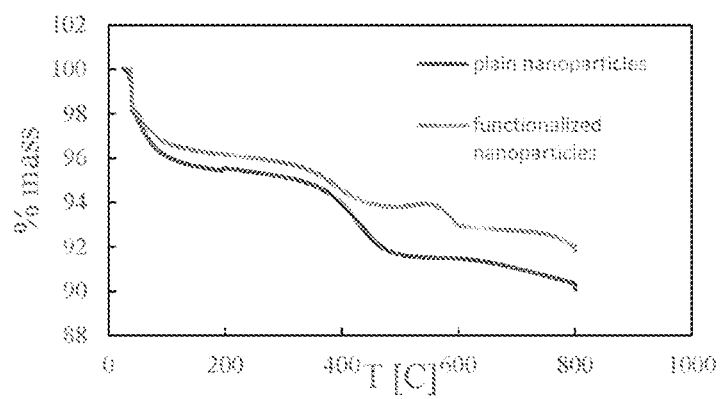
FIG. 22 is a graph showing TGA analysis of the silica coated iron oxide nanoparticles functionalized with hexane.

The nanoparticles were also analyzed by thermogravimetric analysis (TGA) and the results are shown in FIG. 22. For both the non-functionalized and functionalized nanoparticles, the mass decreases when the temperature is increased. Nevertheless, the two signals differ at around 500 C. These results suggest that the grafted silane represent around 1% of the mass of the nanoparticles. However, quantifying accurately the degree of functionalization with FTIR and TGA reveals quite challenging due to the small mass of grafted silane with respect to the mass of the nanoparticle.

Figure 23:
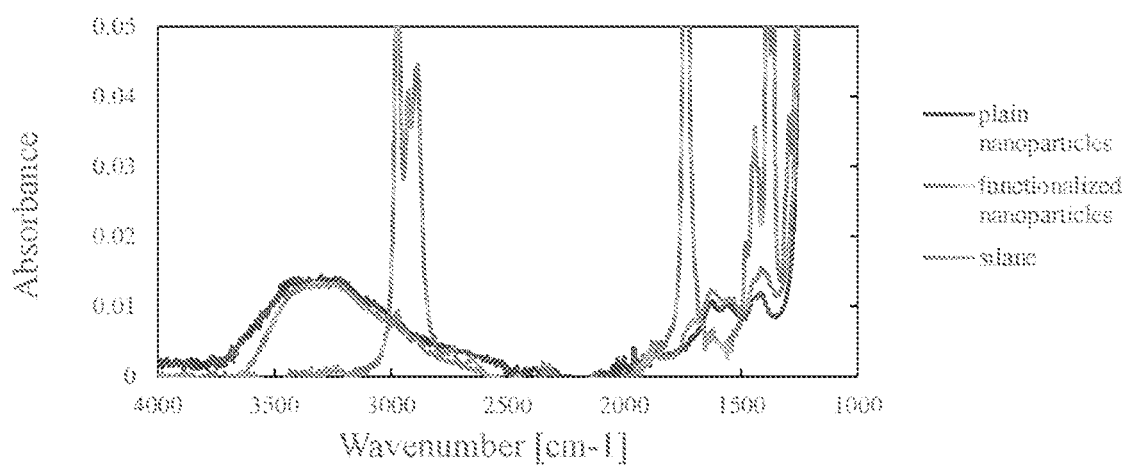
FIG. 23 is a graph showing the FTIR spectrum of silica coated iron oxide nanoparticles functionalized with ethyl acetate. As a comparison, the FTIR spectra of the plain nanoparticles and of the silane are also shown.

The protocol described above is also suitable for the functionalization with SID2665.0, SIC2445.0 and SIM6492.7. However, some adjustments have been made for the functionalization with SIA0025.0 to prevent ester hydrolysis. The water-ethanol mixture is replaced by isopropanol. The FTIR results are shown in FIG. 23. The peak at 3000 cm$^{-1}$ corresponds to the stretching of the C—H bond, whereas the peak at 1700 cm$^{-1}$ corresponds to the C=O bond. These results indicate that functionalization was successful.

Example 15: Diphenhydramine Crystallization with Iron Oxide Nanoparticles (IONPs)

Diphenhydramine hydrochloride (DPH) is shown below:

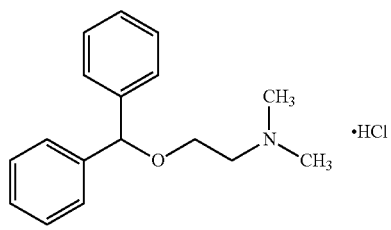 [SMILES: CN(C)CCOC(c1ccccc1)c1ccccc1 ; Cl]

DPH has excellent water solubility, high alcohol solubility, and poor alkane solubility. The solubility of DPH in water is about 400 mg/mL. The solubility of DPH in isopropanol is about 30 mg/mL.

Figure 24:
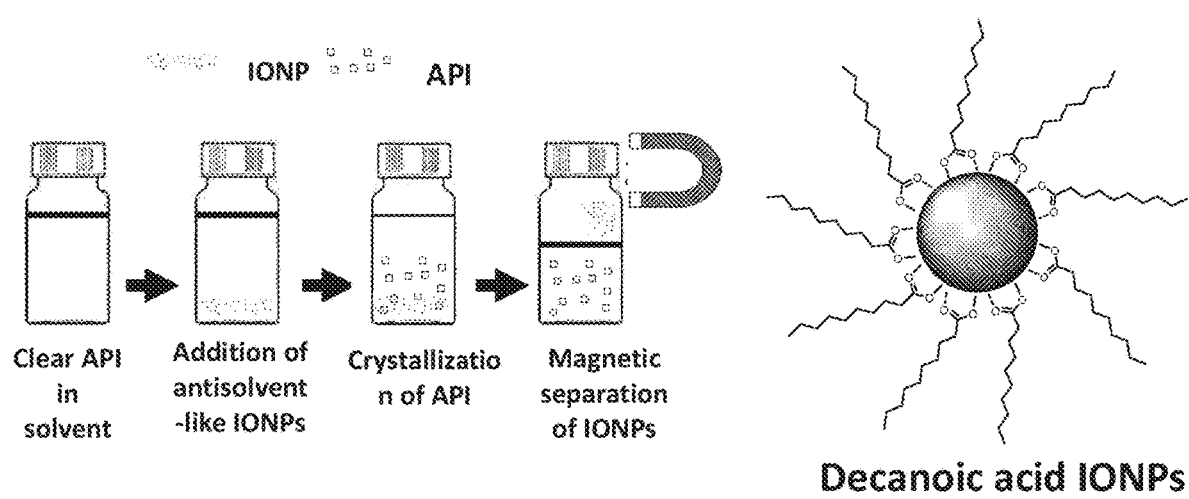
FIG. 24 is a diagram of iron oxide nanoparticles as well as a method for crystallization using the nanoparticles.

A schema for crystallizing DPH using iron oxide nanoparticles (IONPs) shown in FIG. 24. Also shown in FIG. 24 is a schematic illustration of the iron oxide nanoparticles.

Iron oxide nanoparticles were added to DPH in a solvent. The nanoparticles were separated from the solution allowing observation of crystal formation.

Figure 25:
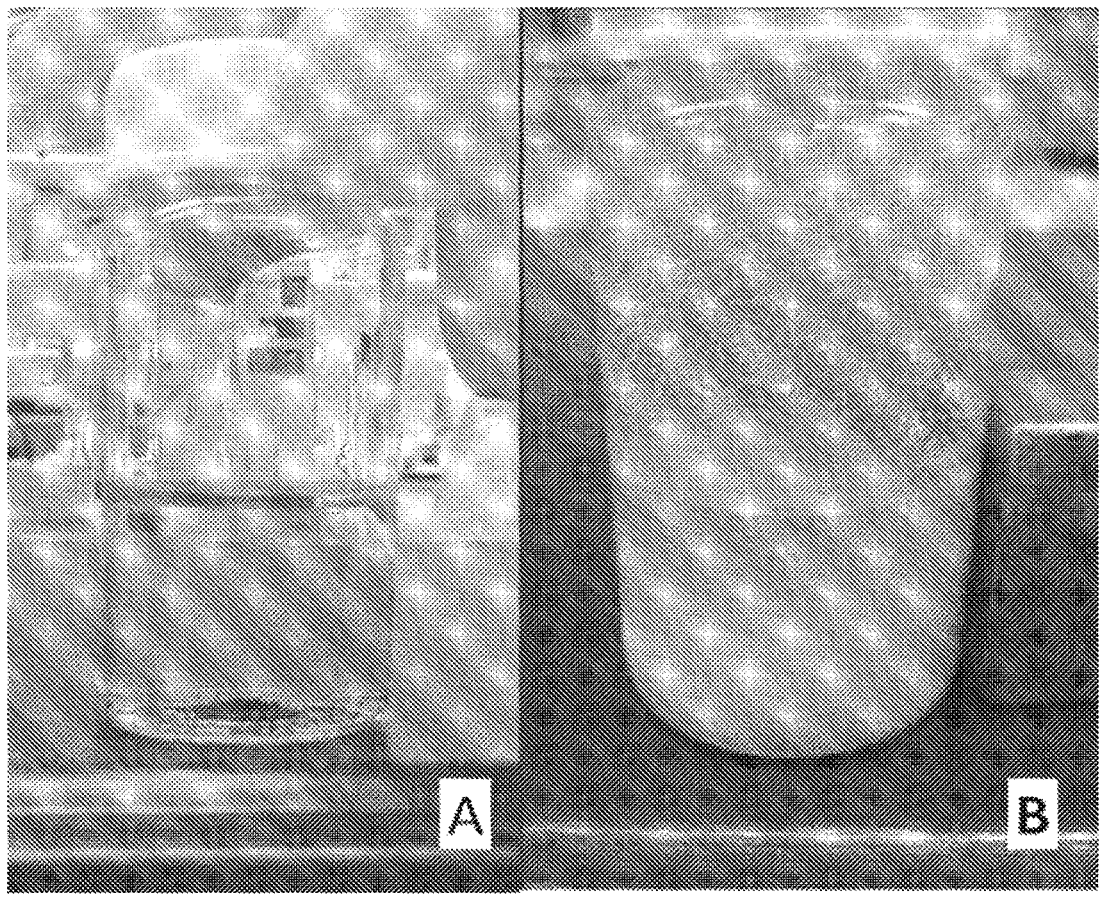
FIGS. 25A and 25B are images of a solution of DPH in isopropanol before incubation with nanoparticles (FIG. 25A) and after incubation with nanoparticles (FIG. 25B).
Figure 26:
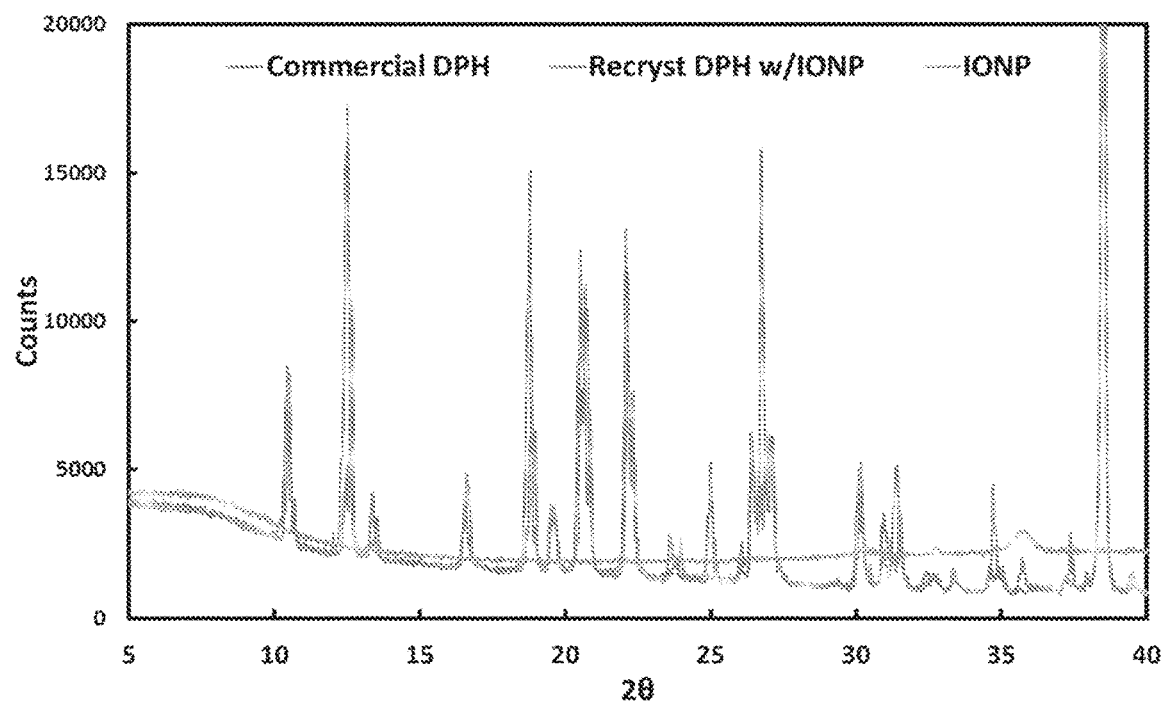
FIG. 26 is a graph showing X-ray diffraction data for DPH before and after crystallization.

The nanoparticles used had decane-like functional groups from decanoic acid. When water was used as a solvent, crystals did not form because the DPH-water supersaturated solution was very stable. However, when isopropanol was used as a solvent, crystallization occurred in about 15 minutes. FIG. 25 shows the isopropanol solution before (FIG. 25A) and after (FIG. 25B) crystallization of DPH using 2.0 mg nanoparticles/mL for 15 minutes. FIG. 26 shows X-ray diffraction results from DPH before and after crystallization demonstrating that that DPH shows no changes upon recrystallization with IONPs.

Example 15. Diphenhydramine Solubilization Using Nanoparticles

Figure 27:
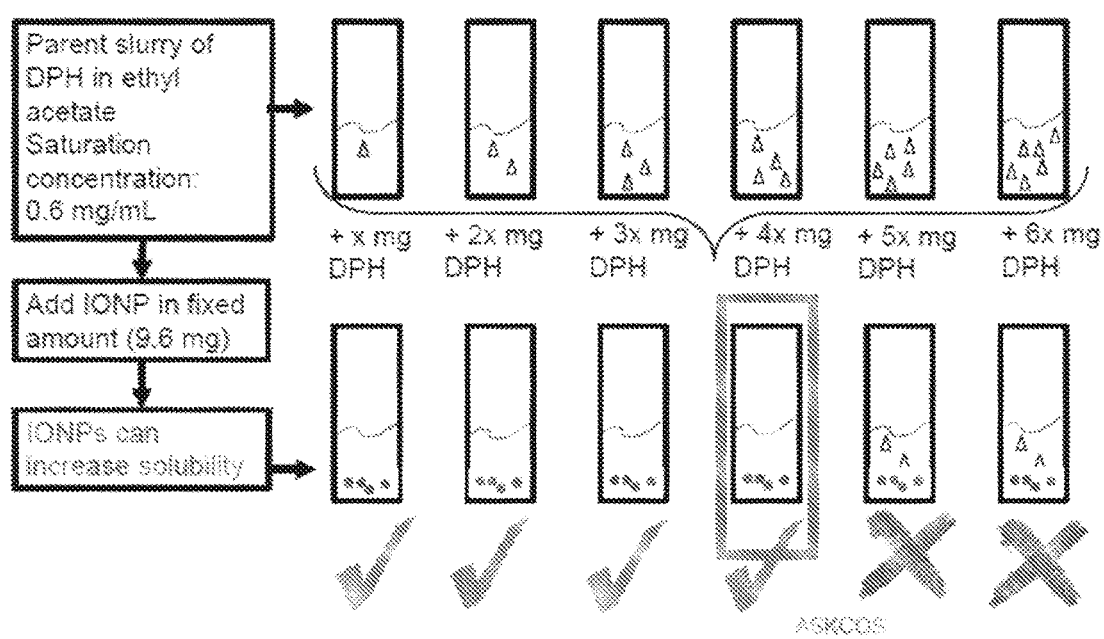
FIG. 27 is a diagram of an experiment for assessing the solubility of DPH in ethyl acetate after addition of nanoparticles.

As is shown in FIG. 27, iron oxide nanoparticles with glycolic acid functional groups, which have an ethanol like chain, were added to a slurry of DPH in ethyl acetate. The functionalized nanoparticles increased the solubility of the nanoparticles. The results are presented in Table 9 below. When approximately 16 mg IONP/mg was added to increase solubility, the result show solubility increased approximately 50% at room temperature. Solubility could be increased further if more IONP/mg were added.

TABLE 9

Solubilization of DPH with iron oxide nanoparticles

| Attempt 1 | | Attempt 2 | |
|---|---|---|---|
| DPH in ethyl acetate percent above saturation | DPH dissolved after IONP addition? | DPH in ethyl acetate Supersaturation | DPH dissolved after IONP addition? |
| 7% | Yes | 9% | Yes |
| 23% | Yes | 20% | Yes |
| 28% | Yes | 25% | Yes |
| 38% | Yes | 42% | Yes |
| 45% | Yes | 52% | Yes |
| 62% | No | 63% | No |
| 73% | No | 72% | No |
| 80% | No | 82% | No |
| 92% | No | 90% | No |

Example 16: Ibuprofen Solubilization Using Nanoparticles

A saturated solution of ibuprofen in water was prepared at room temperature. The solubility of ibuprofen as measured by HPLC in the water was 9.0 jag/mL. An additional 20 mg of ibuprofen was added to 5 mL of the saturated solution. Then, 200 mg of iron oxide nanoparticles that had been functionalized with glycolic acid were added and mixed. Clear samples of solution were then taken from the slurry and analyzed with HPLC. The HPLC data indicated that the solubility was increased to 290 µg/mL.

EQUIVALENTS

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of altering a solution, the method comprising combining, at a temperature, a solution with a readily retrievable agent having one or more functional groups coated or attached to the agent configured to undergo a solvation interaction with a component of the solution, wherein the solvation interaction occurs while the readily retrievable agent is present in the solution at the temperature, and wherein the solvation interaction is solvation of a solute of the solution by the one or more functional groups.

2. The method of claim 1, wherein the solvation interaction is solvation of the one or more functional groups by a solvent.

3. The method of claim 1, wherein the readily retrievable agent is a nanoparticle.

4. The method of claim 3, wherein the nanoparticle is magnetic.

5. The method of claim 1, wherein the readily retrievable agent is surface coated with the one or more functional groups.

6. The method of claim 1, wherein the readily retrievable agent further comprises one or more affinity tags.

7. The method of claim 6, wherein at least one of the one or more affinity tags comprises a streptavidin or biotin moiety.

8. The method of claim 1, further comprising:
   i) maintaining the combination for a period of time; and
   ii) following step i), retrieving the readily retrievable agent from the solution.

9. A method of increasing solution solubility for a compound of interest, the method comprising:
   adding, at a temperature, to a solution comprising the compound of interest, nanoparticles surface coated with functional groups that increase the solution solubility for the compound of interest, wherein following addition of the nanoparticles to the solution at the temperature, the solution solubility for the compound of interest increases to an undersaturated state at the temperature.

10. The method of claim 9, wherein the nanoparticles are removed to reverse the solution solubility for the compound of interest to a saturated or supersaturated state.

* * * * *